(12) United States Patent
Yu et al.

(10) Patent No.: US 10,736,920 B2
(45) Date of Patent: Aug. 11, 2020

(54) PDL1 BLOCK CAR-T TRANSGENIC VECTOR FOR SUPPRESSING IMMUNE ESCAPE, PREPARATION METHOD THEREOF, AND APPLICATION OF THE SAME

(71) Applicant: SHANGHAI UNICAR-THERAPY BIO-MEDICINE TECHNOLOGY CO., LTD, Shanghai (CN)

(72) Inventors: Lei Yu, Shanghai (CN); Liqing Kang, Shanghai (CN); Zhou Yu, Shanghai (CN)

(73) Assignee: SHANGHAI UNICAR-THERAPY BIO-MEDICINE TECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 16/464,682

(22) PCT Filed: Nov. 13, 2017

(86) PCT No.: PCT/CN2017/110656
§ 371 (c)(1),
(2) Date: May 28, 2019

(87) PCT Pub. No.: WO2018/103503
PCT Pub. Date: Jun. 14, 2018

(65) Prior Publication Data
US 2019/0290693 A1 Sep. 26, 2019

(30) Foreign Application Priority Data
Dec. 5, 2016 (CN) .......................... 2016 1 1103294

(51) Int. Cl.
*A61K 39/21* (2006.01)
*C07H 21/04* (2006.01)
*C12N 15/00* (2006.01)
*C12N 15/63* (2006.01)
*A61K 35/17* (2015.01)
*A61K 39/395* (2006.01)
*C07K 16/28* (2006.01)
*C12N 15/86* (2006.01)
*C12N 15/867* (2006.01)
*A61K 48/00* (2006.01)
*A61P 35/00* (2006.01)
*C12N 15/85* (2006.01)

(52) U.S. Cl.
CPC ............ *A61K 35/17* (2013.01); *A61K 39/395* (2013.01); *A61K 48/00* (2013.01); *A61P 35/00* (2018.01); *C07K 16/2818* (2013.01); *C07K 16/2827* (2013.01); *C12N 15/86* (2013.01); *C12N 15/867* (2013.01); *C07H 21/04* (2013.01); *C07K 2317/24* (2013.01); *C12N 2015/8518* (2013.01); *C12N 2820/55* (2013.01); *C12N 2820/60* (2013.01); *C12N 2830/001* (2013.01); *C12N 2830/85* (2013.01)

(58) Field of Classification Search
CPC .... A61K 39/395; C12N 15/86; C12N 15/867; C12N 2820/55; C12N 2820/60; C12N 2830/001; C07H 21/04
USPC ........... 435/320.1, 440; 424/207.1; 536/23.5, 536/24.1
See application file for complete search history.

(56) References Cited

FOREIGN PATENT DOCUMENTS

| CN | 105602992 A | 5/2016 |
|----|-------------|--------|
| WO | 2016026854 A2 | 2/2016 |

OTHER PUBLICATIONS

Genbank accession No. KF732845.1, Genbank, Jun. 24, 2014.
Burnet FM. et al. Immunological Aspects of Malignant Disease. The Lancet, Jun. 3, 1967:1:1171-4.
Ishida Y, et al. Induced Expression of PD-1, a Nove Member of the Immunoglobulin Gene Superfamily, upon Programmed Cell Death. The EMBO Journal, 1992, 11(11):3887-3895.
Li Ying, et al. Advances in PD-1/PD-L1 Signaling Pathway in Tumor Immune Evasion and Its Clinical Significance, Acad J Chin PLA Med Sch, Jul. 2015, 36(7).
Intlekofer AM, et al. At the Bench: Preclinical Rationale for CTLA-4 and PD-1 Blockade as Cancer Immunotherapy, Journal of Leukocyte Biology, Jul. 2013, 94(1):25-39.
Ding H, et al. Delivering PD-1 Inhibitory Signal Concomitant with Blocking ICOS Co-stimulation Suppresses Lupus-like Syndrome in Autoimmune BXSB Mice, Clinical Immunology, 2006, 118(2/3): 258-267.

(Continued)

Primary Examiner — Shin Lin Chen
(74) Attorney, Agent, or Firm — Bayramoglu Law Offices

(57) ABSTRACT

A PDL1 block CAR-T transgenic vector for suppressing immune escape includes: AmpR sequence containing ampicillin resistance gene (SEQ ID NO: 1); prokaryotic replicon pUC Ori sequence (SEQ ID NO: 2); virus replicon SV40 Ori sequence (SEQ ID NO: 3); eWPRE enhanced posttranscriptional regulatory element of hepatitis B virus (SEQ ID NO: 11); human EF1a promoter (SEQ ID NO: 12); lentiviral packaging cis-elements for lentiviral packaging; humanized single-chain antibody fragment PDL1scFv1 (SEQ ID NO: 21), PDL1scFv2 (SEQ ID NO: 22), or PDL1scFv3 (SEQ ID NO: 23) of human PDL1; IRES ribosome binding sequence (SEQ ID NO: 25); IL6 signal peptide (SEQ ID NO: 26); human antibody Fc segment (SEQ ID NO: 27); and chimeric antigen receptors of the second or third generation CAR for integrating recognition, transmission and initiation. A preparation method of the PDL1 block CAR-T transgenic vector and an application thereof in a preparation of anti-immune escape drugs.

20 Claims, 15 Drawing Sheets
Specification includes a Sequence Listing.

(56) References Cited

OTHER PUBLICATIONS

Dong H, et al. Tumor-associated B7-H1 Promotes T-cell Apoptosis:a Potential Mechanism of Immune Evasion. Nature Medicine, Aug. 2002, 8(8):793-800.

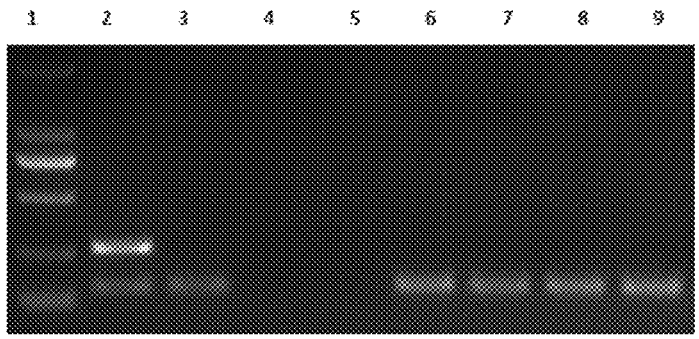

| PCR template | Products of PCR | Judgment and description |
|---|---|---|
| Positive control | a 280bp band and a 150bp band | Established positiveness |
| | no or only one band | Unestablished positiveness |
| Negative control | a 150bp band | Established negativeness |
| | no or more than 2 bands | Unestablished negativeness |
| Sample | a 280bp band and a 150bp band | Mycoplasma contamination |
| | only a 280bp band | Severe mycoplasma contamination |
| | only a 150bp band | No mycoplasma contamination |
| | no band | Insufficient quantity of cells or inhibited PCR |

FIG. 9

| Name of Sample | Actin (CT) | CAR (CT) | -ΔCt | -ΔΔCt | $2^{-\Delta\Delta Ct}$ |
|---|---|---|---|---|---|
| lvCARmm-PDL1scFv1 | 21.96991 | 28.38894 | -6.41904 | 6.20689 | 73.86839 |
| lvCARmm-PDL1scFv2 | 21.93693 | 28.34847 | -6.41154 | 6.21438 | 74.2533 |
| lvCARmm-PDL1scFv3 | 21.83004 | 28.33716 | -6.50712 | 6.1188 | 69.49311 |
| lvCARmm-scFv0 | 21.8691 | 28.39064 | -6.52153 | 6.10439 | 68.80238 |
| MOCK | 22.32917 | 34.4809 | -12.1517 | 0.47419 | 1.389141 |
| Blank | 22.35324 | 34.97916 | -12.6259 | 0 | 1 |

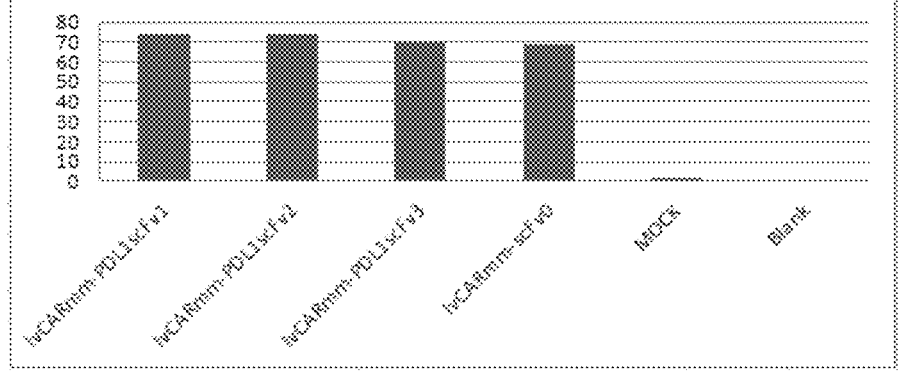

FIG. 10A

| Name of Sample | Actin (CT) | PD1 (CT) | -ΔCt | -ΔΔCt | $2^{-\Delta\Delta Ct}$ |
|---|---|---|---|---|---|
| Blank | 18.31759 | 35.12467 | -16.8071 | 0.397404 | 1.317136 |
| Mock | 17.62152 | 34.82601 | -17.2045 | 0 | 1 |
| lvCARmm-PDL1scFv1 | 18.86972 | 29.87286 | -11.0031 | 6.201344 | 73.58519 |
| lvCARmm-PDL1scFv2 | 18.70974 | 29.81805 | -11.1083 | 6.096176 | 68.41194 |
| lvCARmm-PDL1scFv3 | 17.49874 | 28.53645 | -11.0377 | 6.166781 | 71.84326 |
| lvCARmm-scFv0 | 18.74419 | 29.96707 | -11.2229 | 5.981603 | 63.18907 |

| Name of Sample | Actin (CT) | IL2 (CT) | -ΔCt | -ΔΔCt | $2^{-\Delta\Delta Ct}$ |
|---|---|---|---|---|---|
| Blank | 20.27238 | 30.94715 | -10.6748 | -0.29417 | 0.815539 |
| Mock | 20.55099 | 30.9316 | -10.3806 | 0 | 1 |
| lvCARmm-PDL1scFv1 | 20.09635 | 23.55382 | -3.45746 | 6.92314 | 121.3592 |
| lvCARmm-PDL1scFv2 | 19.79839 | 24.27678 | -4.47839 | 5.90221 | 59.80566 |
| lvCARmm-PDL1scFv3 | 19.89128 | 25.1854 | -5.29412 | 5.086483 | 33.97892 |
| lvCARmm-scFv0 | 20.14015 | 27.34634 | -7.20519 | 3.175413 | 9.034392 |

PDL1 BLOCK CAR-T TRANSGENIC VECTOR FOR SUPPRESSING IMMUNE ESCAPE, PREPARATION METHOD THEREOF, AND APPLICATION OF THE SAME

CROSS REFERENCE TO THE RELATED APPLICATIONS

This application is the national phase entry of International Application No. PCT/CN2017/110656, filed on Nov. 13, 2017, which is based upon and claims priority to Chinese Patent Application No. 201611103294.6, filed on Dec. 5, 2016, the entire contents of which are incorporated herein by reference.

TECHNICAL FIELD

This invention belongs to the field medical biology, specifically relating to a vector, especially a PDL1 block CAR-T transgenic vector for suppressing immune escape. Also, this invention relates to the preparation method and application of the vector.

BACKGROUND

The theoretical basis of tumor immunotherapy is that the immune system can identify tumor-associated antigens and regulate the body to attack tumor cells (highly specific cytolysis). In the 1950s, Burnet and Thomas made the theory of "immunological surveillance" that holds that mutational tumor cells that often occur in the body can be identified and eliminated by the immune system, laying a theoretical foundation for tumor immunotherapy [Burnet F M. Immunological aspects of malignant disease. Lancet, 1967; 1: 1171-4]. Then, a host of tumor immunotherapies, including cytokine therapy, monoclonal antibody therapy, adoptive immunotherapy and vaccine therapy, have been applied to clinical practice.

In 2013, CAR-T, a more advanced tumor immunotherapy, was successfully put to clinical use, and showed unprecedented clinical effects. CAR-T is short for Chimeric Antigen Receptor T-Cell Immunotherapy. Clinically, the most leading CAR-T is Novartis' CLT019. For patients with refractory-relapsed acute lymphoblastic leukemia and treated with CLT019, the six-month tumor progression-free survival rate can reach 67%, and the longest response time can be more than two years. By cooperating with hospitals, Shanghai Unicar-Therapy Bio-Medicine Technology Co., Ltd., a Shanghai-based company, treated 36 patients with refractory-relapsed acute lymphoblastic leukemia, among whom 24 as a percentage of 66.6% experienced complete remission. It's a subversive breakthrough in anti-cancer research. CAR-T may be one of the therapies that are the most likely to cure cancer, and was named the best in top 10 breakthroughs of science and technology 2013 by the journal Science.

Although CAR-T therapy is effective, it encounters many difficulties in the treatment of solid tumors. One of the important reasons is PD1/PDL1 immunosuppressive check points (as shown in FIG. 1A), which combine with the transmission of suppressive signals, inhibit the immunological activity of T cells, play an important role in immunological tolerance, and also promote the escape of tumor cells.

PD-1 (also known as CD279) is an immunosuppressive receptor, belonging to type I transmembrane protein of CD28 family members. Programmed cell death molecule-1 receptor was obtained and named by Ishida et al. in 1992 [Ishida Y, Agata Y, Shibahara K, et al. Induced expression of PD-1, a novel member of the immunoglobulin gene superfamily, upon programmed cell [J]. EMBO J, 1992, 11 (11): 3887-3895.] in apoptotic T cell hybridoma by subtractive hybridization. Human PD-1 gene is located on chromosome 2q37.35 and encodes a transmembrane glycoprotein of about 55 kD. PD-1 is widely expressed on the surface of activated T cells, B cells, monocytes and dendritic cells. The structure of PD-1 shares 30% homology with CTLA-4. There are two tyrosine residues in the intracellular domain, which are involved in the formation of an immunereceptor tyrosine-based inhibitory motif (ITIM) at the N-terminal and an immunoreceptor tyrosin-based switch motif (ITSM) at the C-terminal respectively. The extracellular domain consists of an IgV-like domain, which contains multiple glycosylation sites and is heavily glycosylated. The domain can bind to ligands, thus exerting the function of inhibiting T cell activation [Li Ying, Jiao Shunchang, et al. The role and clinical significance of PD-1/PD-L1 signaling pathway in tumor immune escape [J]. Acad J Chin PLA Med Sch, July 2015, 36 (7)].

PD-L1 is overexpressed in most cancer tissues, including NSCLC, melanoma, breast cancer, glioma, lymphoma, leukemia and various urinary, digestive and reproductive tumors [Intlekofer A M, Thompson C B. At the bench: preclinical rationale for CTLA-4 and PD-1 blockade as cancer immunotherapy[J]. J Leukoc Biol, 2013, 94(1):25-39.]. Parsa found that abnormal IFN-γ secreted by T cells in tumor cells of rats and humans could induce high expression of PD-L1 [Ding H, Wu X, Wu J, et al. Delivering PD-1 inhibitory signal concomitant with blocking ICOS co-stimulation suppresses lupus-like syndrome in autoimmune BXSB mice[J]. Clin Immunol, 2006, 118(2/3):258-267. The high expression of PD-L1 can regulate the expression of cell cycle check point protein and cell proliferation-related protein by inhibiting RAS and PI3K/AKT signaling pathway, and ultimately lead to the inhibition of T cell proliferation [11]. Dong et al. in vitro experiments and mouse models also found that activation of PD-1/PD-L1 signaling pathway can induce specific CTL apoptosis, reduce the sensitivity of CTL to cytotoxicity and induce immune escape of tumor cells [Dong H, Strome S E, Salomao D R, et al. Tumor-associated B7-H1 promotes T-cell apoptosis: a potential mechanism of immune evasion[J]. Nat Med, 2002, 8(8): 793-8001

At present, commercial PD1 monoclonal antibodies are mainly used as immunological check point inhibitors to inhibit the immune escape of cancer cells. On Sep. 3, 2014, Opdivo (Nivolumab), an anti-PD-1 drug from Bristol-Myers Squibb, was officially launched in Japan. The drug is still limited to melanoma patients in Japan. The drug is set at the price of 729849 yen (about 43000 yuan) per 100 mg. Because each 1 kg need 2 mg, people who weigh 50 kg need 100 mg. In addition, every 10 kg increase in body weight required an increase of 20 mg (150200 yen, about 8778 yuan), every three weeks for a course of treatment. The price is so expensive that ordinary families can't afford it.

Therefore, how to use low-cost methods to inhibit the occurrence of immune escape of cancer cells without affecting the efficacy of CAR-T treatment has become a technical problem of CAR-T treatment.

SUMMARY

One of the technical problems to be solved by the invention is to provide a CAR-T transgene vector for suppressing immune escape by blocking PDL1. First of all, it saves the cost and the expensive cost of purchasing antibody drugs. Secondly, it avoids the problem of low delivery efficiency of scFv gene in vivo. Thirdly, the PDL1scFv gene transduced by lentivirus can effectively utilize the intracellular protein translation system and express a large number of corresponding PDL1scFv. Through fluid circulation, good PDL1 blocking effect can be achieved, without affecting the curative effect of CAR-T treatment.

The second technical problem to be solved by the invention is to provide a preparation method of the vector.

The third technical problem to be solved by the invention is to provide the application of the vector.

To solve the above technical problems, the invention adopts the following technical scheme: In one aspect of the invention, a CAR-T transgenic vector for suppressing immune escape by blocking PDL1 is provided, including:

AmpR sequence of ampicillin-resistant gene was amplified for the target bacterial strain, as shown in SEQ ID NO: 1;

Prokaryotic replicon pUC Ori sequence for plasmid replication, as shown in SEQ ID NO: 2; SV40 Ori sequence of viral replicator used to enhance replication in eukaryotic cells, as shown in SEQ ID NO: 3;

eWPRE enhanced posttranscriptional regulatory element of Groundhog hepatitis B virus for enhancing the expression efficiency of transgene, as shown in SEQ ID NO: 11;

Human EF1α promoter for eukaryotic transcription of chimeric antigen receptor genes, as shown in SEQ ID NO: 12;

Lentivirus packaging cis-elements for lentivirus packaging;

The humanized single chain antibody fragment of human PDL1 is PDL1scFv1 as shown in SEQ ID NO: 21, or PDL1scFv2 as shown in SEQ ID NO: 22, or PDL1scFv3 as shown in SEQ ID NO: 23;

IRES ribosome binding sequence for co-transcription and expression of proteins, as shown in SEQ ID NO: 25;

IL6 signal peptide, as shown in SEQ ID NO: 26;

Human antibody Fc segment, as shown in SEQ ID NO: 27;

And chimeric antigen receptors for the second or third generation of CAR, which integrates recognition, transmission and initiation.

As the preferred technical scheme of the invention, the humanized single chain antibody fragment of the human PDL1 is PDL1scFv1 as shown in SEQ ID NO: 21.

The cis-component of the lentivirus packaging can adopt the second generation lentivirus vector or the third generation lentivirus vector, and the third generation lentivirus vector can be optimized. The second generation lentivirus vector includes: lentivirus 5 terminal LTR as shown in SEQ ID NO: 5, lentivirus 3 terminal Self-Inactivating LTR as shown in SEQ ID NO: 6, Gag cis-element as shown in SEQ ID NO: 7, RRE cis-element as shown in SEQ ID NO: 8, env cis-element as shown in SEQ ID NO: 9, cPPT cis-element as shown in SEQ ID NO: 10. The third-generation lentiviral vectors include: lentivirus 5 terminal LTR as shown in SEQ ID NO: 5, lentivirus 3 terminal self-Inactivating LTR as shown in SEQ ID NO: 6, Gag cis-element as shown in SEQ ID NO: 7, RRE cis-element as shown in SEQ ID NO: 8, env cis-element as shown in SEQ ID NO: 9, cPPT cis-element as shown in SEQ ID NO: 10, and RSV promoter as shown in SEQ ID NO: 4.

As the preferred technical scheme of the invention, the chimeric antigen receptors for the second generation CAR comprising: CD8 leader chimeric receptor signal peptide shown in SEQ ID NO: 13, BCMA single chain antibody fragment light chain VL shown in SEQ ID NO: 14, Optimal Linker C shown in SEQ ID NO: 15, BCMA single chain antibody fragment heavy chain VH shown in SEQ ID NO: 16, CD8 Hinge chimeric receptor hinges as shown in SEQ ID NO: 17, CD8 Transmembrane chimeric receptor transmembrane regions as shown in SEQ ID NO: 18, CD137 chimeric receptor costimulatory factors as shown in SEQ ID NO: 19, and TCR chimeric receptor T cell activation domains as shown in SEQ ID NO: 20. The chimeric antigen receptors for the three generations of CAR, which are used for recognition, transmission and initiation, include CD8 leader chimeric receptor signal peptide shown in SEQ ID NO: 13, BCMA single chain antibody fragment light chain VL shown in SEQ ID NO: 14, Optimal Linker C shown in SEQ ID NO: 15, BCMA single chain antibody fragment heavy chain VH shown in SEQ ID NO: 16, CD8 Hinge chimeric receptor hinges shown in SEQ ID NO: 17, CD8 Transmembrane chimeric receptor transmembrane region as shown in SEQ ID NO: 18, CD137 chimeric receptor costimulatory factor as shown in SEQ ID NO: 19, TCR chimeric receptor T cell activation domain as shown in SEQ ID NO: 20, and CD28 chimeric receptor costimulatory factor as shown in SEQ ID NO: 28.

As the preferred technical scheme of the invention, the eWPRE enhanced posttranscriptional regulatory element of Groundhog hepatitis B virus has six nucleotide enhanced mutations, specifically g. 396G>A, g. 397C>T, g. 398T>C, g. 399G>A, g. 400A>T, g. 411A>T.

In the second aspect of the invention, a preparation method of the CAR-T transgenic vector for suppressing immune escape by blocking PDL1 is provided, including the following steps:

(1) AmpR sequence containing ampicillin resistance gene as shown in SEQ ID NO: 1, prokaryotic replicon pUC Ori sequence as shown in SEQ ID NO: 2, virus replicon SV40 Ori sequence as shown in SEQ ID NO: 3, lentivirus packaging cis-element for lentivirus packaging, and eWPRE enhanced posttranscriptional regulatory element of Groundhog hepatitis B virus as shown in SEQ ID NO: 11 were stored on lentivirus skeleton plasmid.

(2) The human EF1α promoter as shown in SEQ ID NO: 12 and chimeric antigen receptors of the second or third generation CAR used for recognition, transmission and initiation were combined into the second or third generation CAR design scheme. The recombinant lentivirus plasmids designed by the second or third generation CAR were cloned into lentivirus skeleton plasmids by digestion, ligation and recombination;

(3) The humanized single-chain antibodies PDL1scFv1, PDL1scFv2, or PDL1scFv3, IRES ribosome binding sequence, IL6 signal peptide and human antibody Fc fragment of human PDL1 were cloned into recombinant lentiviral plasmids, and the recombinant lentiviral plasmids pCARmm-PDL1scFv1, pCARmm-PDL1scFv2, or pCARmm-PDL1scFv3 were obtained;

(4) The recombinant lentiviral plasmids pCARmm-PDL1scFv1, pCARmm-PDL1scFv2, or pCARmm-PDL1scFv3 were transfected into HEK293T/17 cells with lentiviral packaging plasmids pPac-GP, pPac-R and membrane protein pEnv-G respectively. After gene transcription in HEK293T/17 cells, the recombinant lentivirus vector packaged successfully will be released into the cell culture supernatant, and the supernatant containing the recombinant lentivirus vector will be collected;

(5) The supernatant of recombinant lentivirus was purified by column purification with filtration, adsorption and elution, and the recombinant lentivirus vectors were obtained respectively.

As the preferred technical scheme of the invention, step (3) starts the expression of the whole CAR gene by human EF1alpha promoter; the CAR protein locates on the surface of cell membrane, recognizes BCMA antigen, stimulates T cell proliferation and cytokine secretion, and activates the expression of downstream signaling pathway; when scFv region binds to BCMA antigen, signal is transmitted to cells through chimeric receptor, which produces a series of biological effects, such as T cell proliferation, increased cytokine secretion, increased secretion of anti-apoptotic protein, delayed cell death, and lysis of target cells; the fusion protein of PDL1scFv and Fc was co-expressed by IRES ribosome binding sequence and secreted to extracellular space under the guidance of IL6 signal peptide. By binding with PDL1, the binding of PD1 and PDL1 was blocked, thus the signal pathway of PD1/PDL1 was blocked and the immune escape was inhibited.

As the preferred technical scheme of the invention, in step (5), the filtration step is to control the volume of supernatant from 200 ml to 2000 ml, the vacuum degree from −0.5 MPA to 0.9 MPA to prevent the loss of vector caused by blockage. The adsorption step is to control the PH value of solution from 6 to 8 and prevent the vector from inactivating due to the change of PH, and the elution step is to control the ionic strength of eluent from 0.5M to 1.0M and prevent the change of ionic strength leading to incomplete elution or inactivation of vector.

In the third aspect of the invention, the application of the above vectors in the preparation of drugs for suppressing immune escape is provided.

Compared with the existing technology, the invention has the following beneficial effects:

The vector skeleton used in the invention is the third generation lentivirus vector (as shown in FIG. 2A) (disclosed in the invention patent "CAR-T transgenic vector based on replication-defective recombinant lentivirus and its preparation method and application" applied on Mar. 17, 2016). The 3'SIN LTR removes the U3 region, eliminates the possibility of self-replication of the lentivirus vector, and greatly improves the security. The cPPT and WPRE elements were added to improve the transduction efficiency and the expression efficiency of the transgene. RSV promoter was used to ensure the continuous and efficient transcription of core RNA in the packaging of lentiviral vectors, and EF1α promoter was used to make CAR gene continuously expressed in human body for a long time.

The third generation lentivirus skeleton plasmid adopted by the invention (which is disclosed in the invention patent "CAR-T transgenic vector based on replication-defective recombinant lentivirus and its preparation method and application" filed on Mar. 17, 2016) uses eWPRE element, which can enhance the polyadenosine of primary transcription products, increase the content of intracellular RNA and enhance the efficiency of gene expression compared with conventional WPRE.

The method of purification of lentivirus vector column adopted by the invention (as shown in FIG. 7) (disclosed in the invention patent "CAR-T transgenic vector based on replication-defective recombinant lentivirus and its preparation method and application" applied on Mar. 17, 2016), is unlike the usual way of ultracentrifugation or high-speed centrifugation. The semi-automatic operation avoids the tedious and errors of manual operation. The recovered lentiviral vectors fully meet the clinical standards in endotoxin, mycoplasma, host DNA residues and other indicators.

The recombinant lentivirus vector system described in the invention (disclosed in the invention patent of "CAR-T transgenic vector based on replication defective recombinant lentivirus and its preparation method and application" filed on Mar. 17, 2016) is the third generation lentivirus vector. The 3'SIN LTR removes the U3 region, eliminates the possibility of self-replication of the lentivirus vector, and greatly improves the security. The cPPT and WPRE elements were added to improve the transduction efficiency and the expression efficiency of the transgene. RSV promoter was used to ensure the continuous and efficient transcription of core RNA in the packaging of lentiviral vectors, and EF1α promoter was used to make CAR gene continuously expressed in human body for a long time.

The Linker design of the scFv segment adopted by the invention (which is disclosed in the invention patent of "CAR-T transgenic vector based on replication-defective recombinant lentivirus and its preparation method and application" filed on Mar. 17, 2016), can significantly improve the secretion of cytokines, the killing effect of CAR-T cells in vitro and the clinical therapeutic effect.

The invention adopts a single chain antibody fragment (scFv) blocking technology for PDL1. The single chain antibody fragment (scFv) is composed of a heavy chain variable region of the antibody and a light chain variable region connected by a short linker of 15 to 20 amino acids. ScFv can retain its affinity to antigen, and has the characteristics of small molecular weight, strong penetration and weak antigenicity.

The design of human PDL1 blocking single chain antibody fragment can effectively overexpress and secrete in T cells, effectively block the binding of PD1 and PDL1, and block the transmission inhibition signal of PD1/PDL1 signaling pathway. In T cell killing experiment, QPCR detection can effectively improve the mRNA transcription level of IL 2, TNFα and IFNγ in T cells, and relieve the inhibition of T cell activation related genes. In the future, PD1/PDL1 signaling pathway can be blocked in vivo to achieve the effect of suppressing immune escape and improving the efficacy of CAR-T cell therapy for solid tumors.

The scFv fragment and the Fc fragment of the antibody used in the invention have been humanized, which can effectively reduce the production of human anti-mouse antibodies (HAMA) in vivo and improve the half-life and the effect of the scFv.

The invention adopts the action mode of PDL1scFv (as shown in FIG. 1B). First of all, it saves the cost and the expensive cost of purchasing antibody drugs. Secondly, it avoids the problem of low delivery efficiency of scFv gene in vivo. Thirdly, the PDL1scFv gene transduced by lentivirus can effectively utilize the intracellular protein translation system and express a large number of corresponding PDL1scFv. Through fluid circulation, good PDL1 blocking effect can be achieved. The invention screens a series of bioinformatics information such as gene sequence and amino acid sequence of PDL1 antibody, predicts the variable regions of heavy and light chains of PDL1scFv, analyses the secondary structure of PDL1scFv combination and its physicochemical properties, determines the affinity constants of PDL1scFv by soluble expression and indirect ELISA, from which selects three scFv for cell function level detection. Finally, PDL1scFv1 was determined as the best choice and could enter the clinical research stage in the future. The recombinant lentivirus vector skeleton of the invention can carry different therapeutic genes and is widely used in the field of adoptive cell therapy. The recombinant lentivirus vector skeleton carrying PDL1scFv gene is used to block PDL1, inhibit the negative immune regulation signaling pathway and thus inhibit the immune escape of tumors. The lentivirus vector of the invention can express BCMA chimeric antigen receptor on human T lymphocyte, guide and activate the killing effect of T lymphocyte on BCMA positive cells, and is used in clinical treatment of multiple myeloma (MM). The expression of scFv of Programmed Cell Death 1 ligand 1 (PDL1) in human T lymphocyte can effectively block PDL1 and block the negative immunoregulatory signaling pathway. It can be used to suppress the immune escape of tumors and improve the therapeutic effect of CAR-T cell immunotherapy.

It can be seen that the recombinant lentivirus vector of the invention can not only provide reliable transgene guarantee for the treatment of multiple myeloma (MM), but also block the immune escape mechanism of tumors, improve the curative effect of CAR-T cell therapy, greatly reduce the medical cost borne by patients, solve the technical problems in the field, and achieve the unexpected technical effect.

The PDL1 single chain antibody fragment expression frame and its gene expression products can be used not only to eliminate or alleviate the immune escape mechanism in the treatment of multiple myeloma (MM) with CAR-T, but also to inhibit the immune escape mechanism in the treatment of tumors such as pancreatic cancer, glioma, myeloma and so on.

BRIEF DESCRIPTION OF THE DRAWINGS

FIG. 4A is a prediction map of the lentiviral skeleton plasmid pLenti-3G Basic2, where lane 1 is the Cla I+BamH I enzyme digestion prediction of pLenti-3G Basic2, and the band is from top to bottom in sequence of 5854 bp; lane 2 is predicted by 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; and FIG. 4B is an enzyme cut agarose gel electrophoresis map of lentiviral skeleton plasmid pLenti-3G Basic2, where lane 1 is the result of Cla I+BamH I enzyme electrophoresis of pLenti-3 G Basic2; lane 2 is the electrophoresis result of 1 KB DNA ladder Marker;

FIG. 5A is a prediction map of the recombinant lentiviral plasmid pCARmm-Basic2, where lane 1 is 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane 2 is Xba I+Xho I enzyme digestion prediction of pCARmm-Basic2, and the bands from top to bottom are: 6839 bp and 1692 bp; and FIG. 5B is the enzyme digestion agarose gel electrophoresis diagram of recombinant lentiviral plasmid pCARmm-Basic2, where lane1 is the electrophoresis result of 1 kb DNA ladder Marker; lane 2 is the Xba I+Xho I enzyme digestion electrophoresis result of pCARmm-Basic2;

FIG. 6A is pCARmm-PDL1scFv1's enzyme prediction map, where lane1 is 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is BsrG I enzyme digestion prediction of pCARmm-PDL1scFv1, and the bands from top to bottom are 9592 bp and 1298 bp; FIG. 6B is enzyme digestion agarose gel electrophoresis of pCARmm-PDL1scFv1, where lane1 is the electrophoretic result of 1 kb DNA ladder Marker, and lane2 is the result of BsrG I enzyme digestion electrophoresis of pCARmm-PDL1scFv 1; FIG. 6C is the enzyme digestion prediction map of pCARmm-PDL1scFv2, where lane1 is 1 kb DNA ladder Marker, and the bands from top to bottom are in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is Sal I enzyme digestion prediction of pCARmm-PDL1scFv2, and the bands from top to bottom are in sequence: 8484 bp, 1588 bp, 818 bp; FIG. 6D is enzyme digestion agarose gel electrophoresis diagram of pCARmm-PDL1scFv2, where lane1 is the electrophoresis result of 1 kb DNA ladder Marker; lane2 is the Sal I enzyme digestion electrophoresis result of pCARmm-PDL1scFv2; FIG. 6E is the diagram is the enzyme digestion prediction map of pCARmm-PDL1scFv3, where lane1 is 1 kb DNA ladder Marker, and the bands are from top to bottom in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is Pvu II enzyme digestion prediction of pCARmm-PDL1scFv3, and bands from top to bottom are in sequence: 3354 bp, 2364 bp, 1920 bp, 1460 bp, 823 bp, 733 bp; FIG. 6F is the enzyme digestion agarose gel electrophoresis of pCARmm-PDL1scFv3, where lane1 is the electrophoresis result of 1 kb DNA ladder Marker, and lane2 is the Pvu II enzyme digestion electrophoresis result of pCARmm-PDL1scFv3; FIG. 6G is the enzyme digestion prediction map of pCARmm-scFv0, where lane1 is 1 kb DNA ladder Marker, and bands from top to bottom are in sequence: 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; lane2 is Kpn I enzyme digestion prediction of pCARmm-scFv0, and the bands from top to bottom are: 7028 bp, 3626 bp, 895 bp, 347 bp; and FIG. 6H is an enzyme digestion agarose gel electrophoresis map of pCARmm-scFv0, where lane1 is the electrophoresis result of 1 kb DNA ladder Marker, and lane2 is the Kpn I enzyme digestion electrophoresis of pCARmm-scFv0;

FIG. 9 is a schematic diagram of mycoplasma detection results of different purification methods of recombinant lentivirus vectors in embodiment 2 of the invention, where lane 1 is DL2000 marker, and the bands from top to bottom in sequence: 2 kb, 1 kb, 750 bp, 500 bp, 250 bp and 100 bp; lane 2 is a positive control; lane 3 is a negative control; lane 4 is PBS; lane 5 is water; lane 6 is 1vCARmm-PDL1scFv1v1; lane 7 is 1vCARmm-PDL1scFv2; lane8 is 1vCARmm-PDL1scFv3; lane9 is 1vCARmm-scFv0;

FIGS. 10A and 10B is a histogram of the relative expression of mRNA in embodiment 3 of the invention, where FIG. 10A is a schematic diagram of RT-QPCR results, indicating that CAR gene is highly transcribed in PBMC cells; and FIG. 10B is a schematic diagram of RT-QPCR results, indicating that scFv gene is highly transcribed in PBMC cells;

in FIG. 11A, M is protein Marker, lane 1 is empty PBMC cell, lane 2 is control virus MOCK, lane 3 is 1vCARmm-PDL1scFv1, lane 4 is 1vCARmm-PDL1scFv2, lane 5 is 1vCARmm-PDL1scFv3, lane 6 is 1vCARmm-scFv0; and FIG. 11B is an internal reference band of beta-actin;

FIG. 15A represents RT-QPCR results, IL-2 gene transcription levels in PBMC cells of each experimental group; FIG. 15B represents RT-QPCR results and TNFα gene transcription levels in PBMC cells of each experimental group; and FIG. 15C represents RT-QPCR results and IFNγ gene transcription levels in PBMC cells of each experimental group.

DETAILED DESCRIPTION OF THE EMBODIMENTS

Figure 1A:
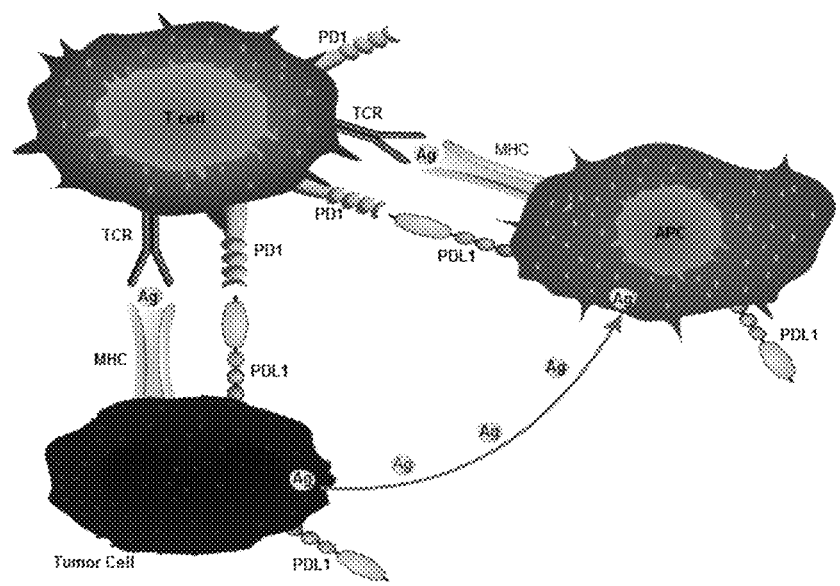
FIG. 1A is a schematic diagram of the PD1/PDL1 signaling pathway of the invention.
Figure 1B:
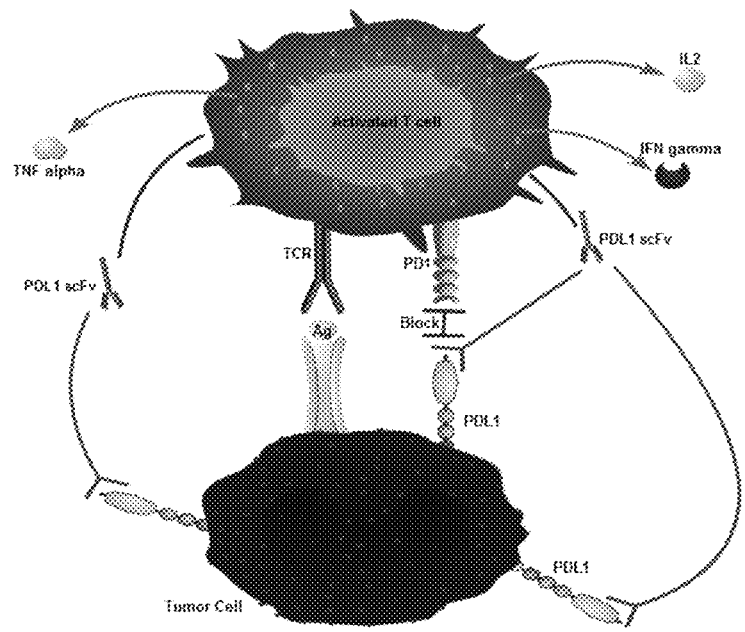
FIG. 1B is a schematic diagram of the mode of action of the PDL1scFv of the invention.
Figure 2A:
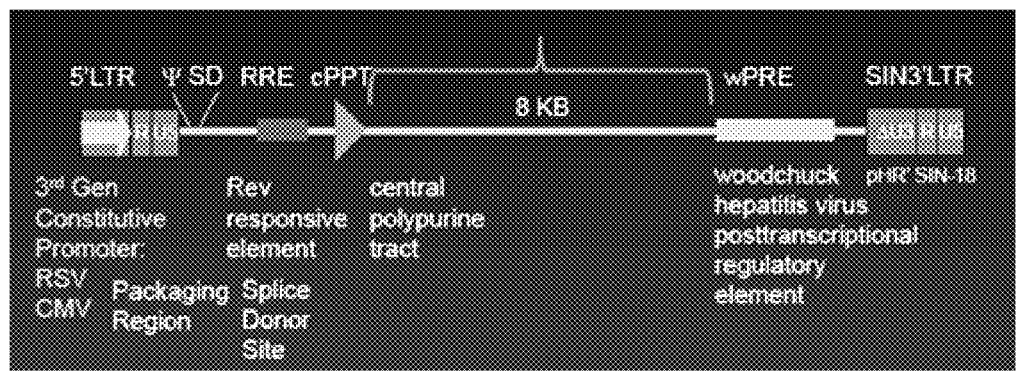
FIG. 2A is a schematic diagram of the structure of the third generation lentiviral vector adopted by the invention.
Figure 2B:
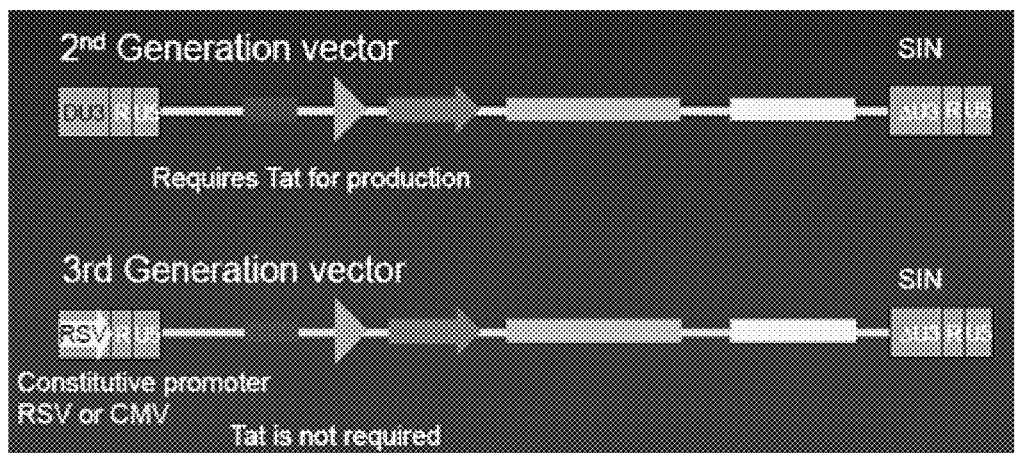
FIG. 2B is a schematic diagram of the structure comparison of the second and third generation lentiviral vectors.

The invention is further described below in connection with specific implementation methods. It should be understood that the specific implementation methods described herein are expressed by way of examples and are not constrained by the invention. Without departing from the scope of the invention, the main features of the invention can be used in various implementation methods.

Embodiment 1 to Construct Recombinant Lentiviral Vector

I. Materials

1. Lentiviral cytoskeleton plasmid pLenti-3 G Basic2, lentiviral packaging plasmid pPac-GP, pPac-R and membrane protein plasmid pEnv-G, HEK293T/17 cells, homologous recombinase, Oligo Annealing Buffer were provided by Shiao (Shanghai) Biotech Co., Ltd.;

2. Primers: Designed according to the principle of primer design, the primers required for amplification of DNA fragments and target sites were synthesized by Shanghai-based biotechnology companies, specifically as follows:

```
EF1α-F:
                                     (SEQ ID NO: 29)
5'-ATTCAAAATTTTATCGATGCTCCGGTGCCCGTCAGT-3'

EF1α-R:
                                     (SEQ ID NO: 30)
5'-TCACGACACCTGAAATGGAAGA-3'

CD8 leader-F:
                                     (SEQ ID NO: 31)
5'-GGTGTCGTGAGGATCCGCCACCATGGCCTTACCAGTGACCGC-3'

CD8 leader-R:
                                     (SEQ ID NO: 32)
5'-GGTCATCTGGATGTCCGGCCTGGCGGCGTG-3'

VL-F:
                                     (SEQ ID NO: 33)
5'-CACGCCGCCAGGCCGGACATCCAGATGACCCAGAGCC-3'

VL-R:
                                     (SEQ ID NO: 34)
5'-ACGCTTGATCTCCAGTTTGGT-3'

OLC-VH-F:
                                     (SEQ ID NO: 35)
5'-ACTGGAGATCAAGCGTGGTGGCGGTGGCTCGGGCGGTGGTGGGTCGG
GTGGCGGCGGATCTCAGGTGCAGCTGGTCCAGAG-3'

VH-R:
                                     (SEQ ID NO: 36)
5'-GCTGGACACGGTCACTAGTGTG-3'

CD8 Hinge-F:
                                     (SEQ ID NO: 37)
5'-AGTGACCGTGTCCAGCACCACGACGCCAGCGCC-3'

CD8 Hinge-R:
                                     (SEQ ID NO: 38)
5'-GTAGATATCACAGGCGAAGTCCA-3'

CD8 Transmembrane-F:
                                     (SEQ ID NO: 39)
5'-CGCCTGTGATATCTACATCTGGGCGCCCTTGGC-3'

CD8 Transmembrane-R:
                                     (SEQ ID NO: 40)
5'-TCTTTCTGCCCCGTTTGCAGTAAAGGGTGATAACCAGTG-3'

CD137-F:
                                     (SEQ ID NO: 41)
5'-AAACGGGGCAGAAAGAAACTC-3'

CD137-R:
                                     (SEQ ID NO: 42)
5'-TGCTGAACTTCACTCTCAGTTCACATCCTCCTTCTTCTTC-3'

TCR-F:
                                     (SEQ ID NO: 43)
5'-AGAGTGAAGTTCAGCAGGAGCG-3'
```

TCR-R:
(SEQ ID NO: 44)
5'-GGAGAGGGGCGTCGACTTAGCGAGGGGGCAGGGC-3'

IRES-F:
(SEQ ID NO: 45)
5'-GCCCTGCCCCCTCGCTAAGCCCCTCTCCCTCCCC-3'

IRES-R:
(SEQ ID NO: 46)
5'-CCAGGGAGAAGGCAACTGGACCGAAGGCGCTTGTGGAGAAGGAGTTC
ATGGTGGCATTATCATCGTGTTTTTCAAAGGA-3'

PDL1s1-F:
(SEQ ID NO: 47)
5'-GTTGCCTTCTCCCTGGGGCTGCTCCTGGTGTTGCCTGCTGCCTTCCC
TGCCCCAGATATTGTGCTGACCCAGAG-3'

PDL1s1-R:
(SEQ ID NO: 48)
5'-GCAGCTTTTCGGTTCGCTGCTCACGGTCACCAGGGT-3'

PDL1s2-F:
(SEQ ID NO: 49)
5'-GTTGCCTTCTCCCTGGGGCTGCTCCTGGTGTTGCCTGCTGCCTTCCC
TGCCCCAGATATTCAGATGACCCAGAGC-3'

PDL1s2-R:
(SEQ ID NO: 50)
5'-GCAGCTTTTCGGTTCGCTGCTCACGGTCACCAGGGT-3'

PDL1s3-F:
(SEQ ID NO: 51)
5'-GTTGCCTTCTCCCTGGGGCTGCTCCTGGTGTTGCCTGCTGCCTTCCC
TGCCCCAGATATTGTGCTGACCCAGAGC-3'

PDL1s3-R:
(SEQ ID NO: 52)
5'-GCAGCTTTTCGGTTCCGCGCTCGCGGTCACCAGGGT-3' s0-F:
(SEQ ID NO: 53)
5'-GTTGCCTTCTCCCTGGGGCTGCTCCTGGTGTTGCCTGCTGCCTTCCC
TGCCCCATTGTTCTGGATTCCTGCTTCCA-3' s0-R:
(SEQ ID NO: 54)
5'-GCAGCTTTTCGGTTCTGCAGAGACAGAGACCAGAGT-3'

Fc-F:
(SEQ ID NO: 55)
5'-GAACCGAAAAGCTGCGATAAAAC-3'

Fc-R:
(SEQ ID NO: 56)
5'-CTAGCAATCTAGAGGTTATTTGCCCGGGCTCAGGCTCA-3'

WPRE-QPCR-F:
(SEQ ID NO: 57)
5'-CCTTTCCGGGACTTTCGCTTT-3'

WPRE-QPCR-R:
(SEQ ID NO: 58)
5'-GCAGAATCCAGGTGGCAACA-3'

Actin-QPCR-F:
(SEQ ID NO: 59)
5'-CATGTACGTTGCTATCCAGGC-3'

Actin-QPCR-R:
(SEQ ID NO: 60)
5'-CTCCTTAATGTCACGCACGAT-3'

CAR-QPCR-F:
(SEQ ID NO: 61)
5'-GACTTGTGGGGTCCTTCTCCT-3'

CAR-QPCR-R:
(SEQ ID NO: 62)
5'-GCAGCTACAGCCATCTTCCTC-3'

PD1-QPCR-F:
(SEQ ID NO: 63)
5'-TGCAGCTTCTCCAACACAT-3'

PD1-QPCR-R:
(SEQ ID NO: 64)
5'-CTTGTCCGTCTGGTTGCT-3'

IL2-QPCR-F:
(SEQ ID NO: 65)
5'-CACCAGGATGCTCACATTTAAGT-3'

IL2-QPCR-R:
(SEQ ID NO: 66)
5'-GTCCCTGGGTCTTAAGTGAAAGT-3'

Fc-QPCR-F:
(SEQ ID NO: 67)
5'-GACATTGGAAATGTGAACATGT-3'

Fc-QPCR-R:
(SEQ ID NO: 68)
5'-CACAGCTGGGGTTTGGTGA-3'

TNFα-QPCR-F:
(SEQ ID NO: 69)
5'-TCTCTAATCAGCCCTCTG-3'

TNFα-QPCR-R:
(SEQ ID NO: 70)
5'-GGGTTTGCTACAACATGG-3'

IFNγ-QPCR-F:
(SEQ ID NO: 71)
5'-GACTAATTATTCGGTAACTGA-3'

IFNγ-QPCR-R:
(SEQ ID NO: 72)
5'-GATGCTCTTCGACCTCGAAACA-3'

3. The DNA sequences shown in SEQ ID NO: 15~SEQ ID NO: 72 were synthesized by Shanghai Generay Biotech Co., Ltd., and stored as oligonucleotide dry powder or plasmid;

4. Tool enzymes Xba I, Xho I, Pvu II, Sal I, BsrG I, BamH I, Kpn I, Cla I and T4 DNA ligases were purchased from NEB;

5. PrimerSTAR HS DNA Polymerase, RN were purchased from Takara;

6. 0.22 μm-0.8 μm PES filters were purchased from millipore;

7. The Plasmid Extraction Kit and Agarose Gel Recovery Kit were purchased from MN;

8. TOP 10 Competent Cell were purchased from tiangen;

9. NaCl, KCl, $Na_2HPO_4.12H_2O$, $KH_2PO_4$, Trypsin, EDTA, $CaCl_2$), NaOH, PEG6000 were purchased from Shanghai Sangon Biotech;

10. Opti-MEM, FBS, DMEM, 1640, Pen-Srep, Hepes were purchased from invitrogen;

11. Biotinylated protein L and proteinG-HRP were purchased from GeneScript;

12. HRP-labeled secondary antibodies and DAB working fluid were purchased from ZSGB-BIO;

13, ECL+plusTM Western blotting system purchased from Amersham;

13. ECL+plusTM Western blotting system was purchased from Amersham;

14. DNeasy kit was purchased from Shanghai Generay Biotech Co., Ltd.;

15. Lymphocyte Separation Medium were purchased from Dakewe Biotech Co., Ltd.;

16. Phycoerythrin (PE)-conjugated streptavidin was purchased from BD Bioscience;

17. SA-HRP, TMB Substrate and ELISA Stop Solution were purchased from Yeasen Biotech Co., Ltd.;

18. Mycoplasma Detection Kit, Endotoxin Detection Kit, BCMA-K562 cells and BCMA-PDL1-K562 cells were purchased from Shiao (Shanghai) Biotech Co., Ltd.;

19. LDH Detection Kit was purchased from promega.

II. Preparation Method of Recombinant Lentiviral Vectors 1vCARmm-PDL1scFv1, 1vCARmm-PDL1scFv2, 1vCARmm-PDL1scFv3, 1vCARmm-scFv0

Figure 3:
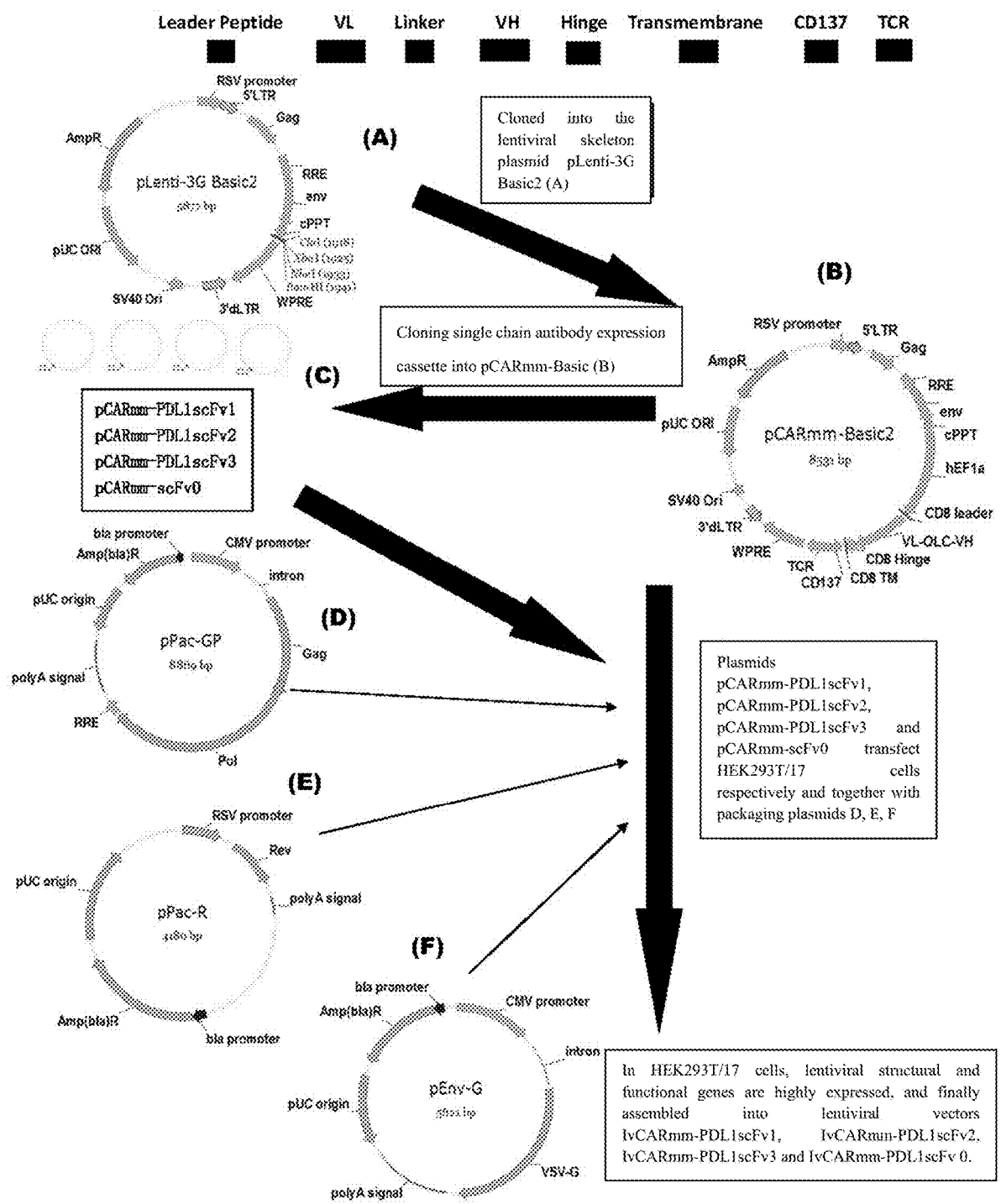
FIG. 3 is a flow chart for constructing the recombinant lentivirus vector in embodiment I of the invention; where part (A) is the structure diagram of the lentivirus skeleton plasmid pLenti-3G Basic2; part (B) is the structure diagram of the pCARmm-Basic2 plasmid; part (C) is the structure diagram of the pCARmm-PDL1scFv1, pCARmm-PDL1scFv2, pCARmm-PDL1scFv3 and pCARmm-scFv0 plasmid; part (D) is the structure diagram of the lentivirus packaging plasmid pPac-GP; part (E) is the structure diagram of the lentivirus packaging plasmid pPac-R; and part (F) is the structure diagram of membrane protein pEnv-G.

See FIG. 3. The preparation method of the recombinant lentiviral vector described in the invention is as follows:

1. The human EF1α promoters, CD8 leader chimeric receptor signal peptide, BCMA single chain antibody light chain VL, Optimal Linker C, BCMA single chain antibody heavy chain VH, CD8 chimeric receptor hinge, CD8 transmembrane domain chimeric receptor, the chimeric receptor co-stimulation factor-CD137, TCR and T cell activation domain chimeric receptor fragments were cloned into the lentiviral cytoskeleton plasmid pLenti-3GBasic2 to obtain recombinant lentiviral plasmid pCARmm-Basic2, and the siRNA fragments were connected into pCARmm-Basic2 respectively to obtain IL-6 know-down recombinant lentiviral plasmid pCARmm-PDL1scFv1, pCARmm-PDL1scFv2, pCARmm-PDL1scFv3 and control pCARmm-scFv0.

Figure 4A:
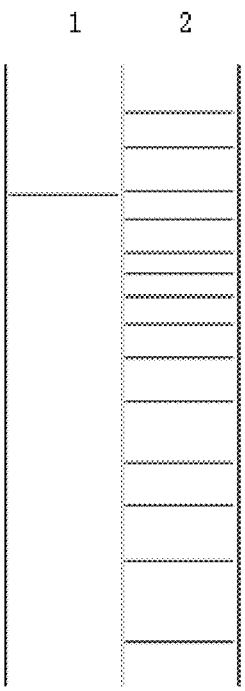
FIGS. 4A and 4B are enzyme digestion prediction and enzyme digestion agarose gel electrophoresis diagrams of the lentivirus skeleton plasmid pLenti-3G Basic2 in the embodiment 1 of the invention; where
Figure 4B:
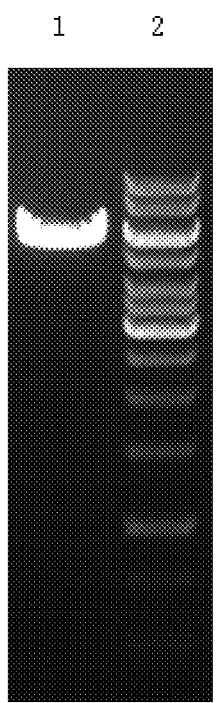

(1) The lentiviral cytoskeleton plasmid pLenti-3G Basic2 was double digested with Cla I and BamH I restriction enzymes. The product was electrophoresed on a 1.5% agarose gel to confirm the 5854 bp fragment V1 (see FIGS. 4A and 4B), then such gel was recovered and placed in an Eppendorf tube. The corresponding fragments were recovered with Agarose Gel Recovery Kit of MN (see Table 1), and the purity and concentration of the product were determined.

TABLE 1

Procedures for the recovery of agarose gels

| | |
|---|---|
| 1. Sol | Add the sol solution in a ratio of 200 μl NTI/100 mg gel, and place it in a 50° C. water bath for 5-10 minutes. |
| 7. Bind to DNA | Centrifuge at 11,000 g for 30 seconds, and discard the filtrate. |
| 8. Wash membrane | Add 700 μl NT3, centrifuge at 11,000 g for 30 seconds, and discard the filtrate |
| 9. Wash membrane | Repeat the third step once |
| 10. Dry | Centrifuge at 11,000 g for 1 minute, replace with a new collection tube, and leave it at room temperature for 1 minute. |
| 11. Elute DNA | Add 15-30 μl NE, leave it at room temperature for 1 minute, centrifuge at 11,000 g for 1 minute, and then collect the filtrate. |

(2) Use the primers EF1α-F and EF1α-R with the synthesized SEQ ID NO: 12 as a template, and apply the system in Table 2. PCR circulation condition was: 98° C. 3 min, (98° C. 10 sec, 55° C. 15 sec, 72° C. 2 min)*35 cycle, 72° C. 10 min. The product was electrophoresed on a 1.5% agarose gel to confirm the 1208 bp fragment a, then such gel was recovered and placed in an Eppendorf tube. The corresponding fragments were recovered with Agarose Gel Recovery Kit of MN (see Table 1), and the purity and concentration of the product were determined.

TABLE 2

50 μl PCR reaction system

| Reagent | Volume (μl) |
|---|---|
| H$_2$O | 32.5 |
| 5 × Buffer (with Mg2+) | 10 |
| dNTP (2.5 mM each) | 4 |
| Primer1 (+)(10 μM) | 1 |
| Primer2 (−)(10 μM) | 1 |
| Template | 1 |
| PrimeSTAR | 0.5 |

(3) Use the primers CD8 leader-F and CD8 leader-R with the synthesized SEQ ID NO: 13 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 101 bp fragment b, then such gel was recovered and placed in an Eppendorf tube. The corresponding fragments were recovered with Agarose Gel Recovery Kit of MN (see Table 1), and the purity and concentration of the product were determined.

(4) Use the primers VL-F and VL-R with the synthesized SEQ ID NO: 14 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 336 bp fragment c, then such gel was recovered and placed in an Eppendorf tube. The corresponding fragments were recovered with Agarose Gel Recovery Kit of MN (see Table 1), and the purity and concentration of the product were determined.

(5) Use the primers OLC-VH-F and VH-R with the synthesized SEQ ID NO: 16 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 421 bp fragment d, then such gel was recovered and placed in an Eppendorf tube. The corresponding fragments were recovered with Agarose Gel Recovery Kit of MN (see Table 1), and the purity and concentration of the product were determined.

(6) Use the primers CD8 Hinge-F and CD8 Hinge-R with the synthesized SEQ ID NO: 17 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 147 bp fragment e, then such gel was recovered and placed in an Eppendorf tube. The corresponding fragments were recovered with Agarose Gel Recovery Kit of MN (see Table 1), and the purity and concentration of the product were determined.

(7) Use the primers CD8 Transmembrane-F and CD8 Transmembrane-R with the synthesized SEQ ID NO: 18 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 100 bp fragment f, then such gel was recovered and placed in an Eppendorf tube. The corresponding fragments were recovered with Agarose Gel Recovery Kit of MN (see Table 1), and the purity and concentration of the product were determined.

(8) Use the primers CD137-F and CD137-R with the synthesized SEQ ID NO: 19 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 142 bp fragment g, then such gel was recovered and placed in an Eppendorf tube. The corresponding fragments were recovered with Agarose Gel Recovery Kit of MN (see Table 1), and the purity and concentration of the product were determined.

(9) Use the primers TCR-F and TCR-R with the synthesized SEQ ID NO: 20 as a template, and apply the system in Table 2. PCR circulation condition was: 98° C. 3 min, (98° C. 10 sec, 55° C. 15 sec, 72° C. 30 sec)*35 cycle, 72° C. 5 min. The product was electrophoresed on a 1.5% agarose gel to confirm the 335 bp fragment h, then such gel was recovered and placed in an Eppendorf tube. The corresponding fragments were recovered with Agarose Gel Recovery Kit of MN (see Table 1), and the purity and concentration of the product were determined.

(10) Applying the system in Table 3, 1μl each of DNA fragments b, c and d were taken as templates to add to Eppendorf tubes except for primers. PCR circulation condition was: 98° C. 3 min, (98° C. 10 sec, 60° C. 10 sec, 72° C. 30 sec)*6 cycle. To add primer CD8 leader-F/VH-R with the conditions as (98° C. 10 sec, 60° C. 10 sec, 72° C. 40 sec)*24 cycle, 72° C. 5 min. The product was electrophoresed on a 1.5% agarose gel to confirm the 814 bp fragment i, then such gel was recovered and placed in an Eppendorf tube. The corresponding fragments were recovered with Agarose Gel Recovery Kit of MN (see Table 1), and the purity and concentration of the product were determined.

TABLE 3

| 50 μl overlapping PCR reaction system | |
| --- | --- |
| Reagent | Volume (μl) |
| H$_2$O | 33.5-1* number of templates |
| 5 × Buffer (with Mg2+) | 10 |
| dNTP (2.5 mM each) | 4 |
| Primer1(+) (10 μM) | 1 |
| Primer2(−) (10 μM) | 1 |
| Template | 1* number of templates |
| PrimeSTAR | 0.5 |

(11) Applying the system in Table 3, 1μl each of DNA fragments e, f, g and h were taken as templates to add to Eppendorf tubes except for primers. PCR circulation condition was: 98° C. 3 min, (98° C. 10 sec, 60° C. 10 sec, 72° C. 30 sec)*6 cycle. To add primer CD8 Hinge-F/TCR-R with the conditions as (98° C. 10 sec, 60° C. 10 sec, 72° C. 30 sec)*24 cycle, 72° C. 5 min. The product was electrophoresed on a 1.5% agarose gel to confirm the 704 bp fragment j, then such gel was recovered and placed in an Eppendorf tube. The corresponding fragments were recovered with Agarose Gel Recovery Kit of MN (see Table 1), and the purity and concentration of the product were determined.

Figure 5A:
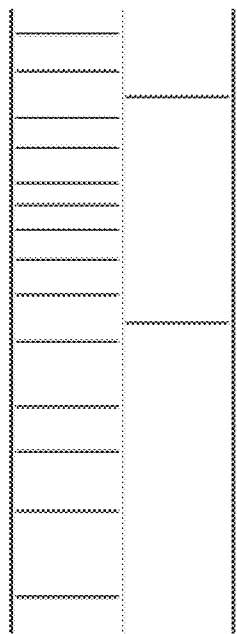
FIGS. 5A and 5B are enzyme digestion prediction and enzyme digestion agarose gel electrophoresis diagrams of recombinant lentiviral plasmid pCARmm-Basic2 in embodiment 1 of the invention; where
Figure 5B:
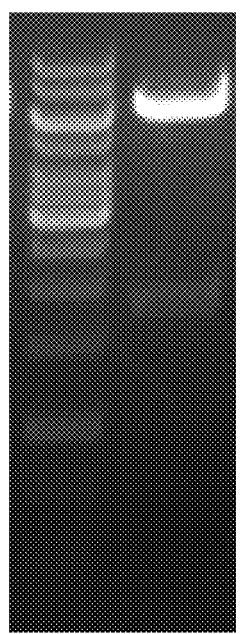
Figure 6A:
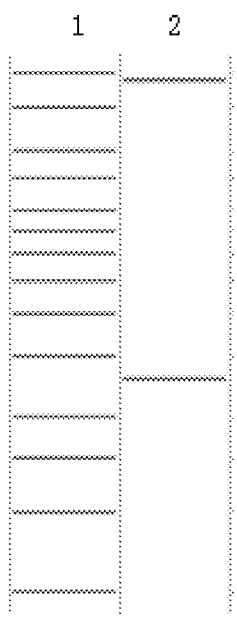
FIGS. 6A-6H are enzyme digestion prediction and enzyme digestion agarose gel electrophoresis diagrams of recombinant lentiviral vectors pCARmm-PDL1scFv1, pCARmm-PDL1scFv2, pCARmm-PDL1scFv3 and pCARmm-scFv0 in the embodiment 1 of the invention; where
Figure 6B:
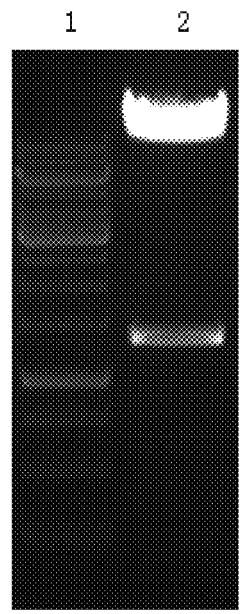
Figure 6C:
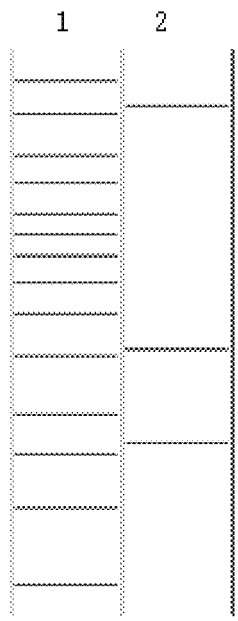
Figure 6D:
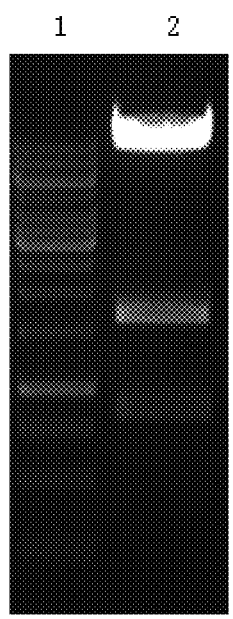
Figure 6E:
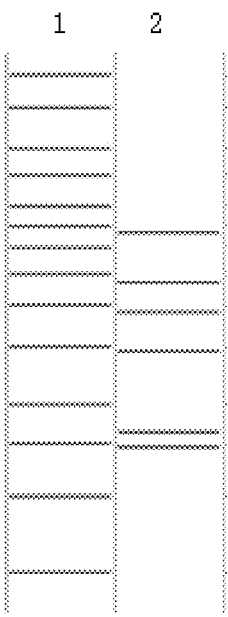
Figure 6F:
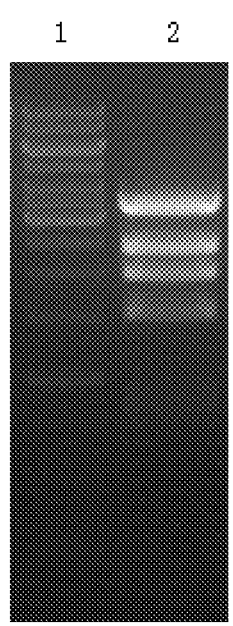
Figure 6G:
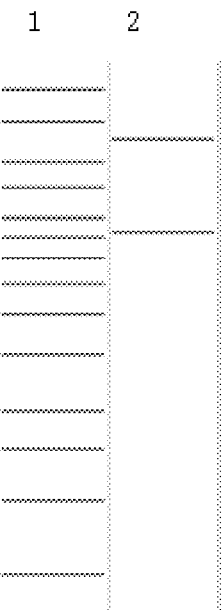
Figure 6H:
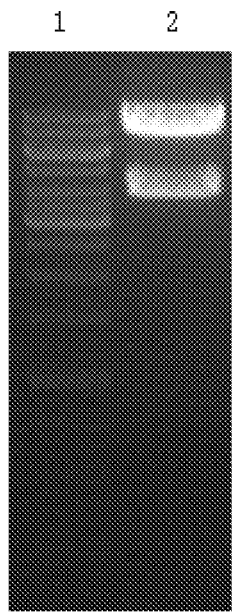

(12) The DNA fragments V1, a, i, j were added to the Eppendorf tubes in a total volume of 5 μl with a molar ratio of 1:1:1:1. 15 μl of the homologous recombinase reaction solution was added to the tubes, and the mixtures were incubated at 42° C. for 30 minutes. Place them on ice for 2-3 minutes. Add the reaction solution to 50 μl of TOP10, gently rotate to mix the contents, place them on ice for 30 minutes, then put the tubes in the thermostatic water bath pre-warmed to 42° C. for 90 seconds, and quickly transfer the tubes in an ice bath. The cells were allowed to cool for 2-3 minutes. Add 900 μl of LB medium to each tube, then put the tubes to a 37° C. shaker and incubate for 1 hour to resuscitate the bacteria. Take 100 μl of transformant bacteria solution to apply to an Amp LB agar plate, invert the plate, and culture in a thermostatic incubator at 37° C. for 16 hours. The clones were picked for colony PCR identification, and the correct clones were identified as recombinant lentiviral plasmid pCARmm-Basic2. Enzyme digestion identification was performed for the correct clones (see FIGS. 5A and 5B).

(13) The recombinant lentiviral plasmid pCARmm-Basic2 was double digested with Sal I and Nhe I restriction enzymes. The product was electrophoresed on a 1.5% agarose gel to confirm the 8491 bp fragment V2, then such gel was recovered and placed in an Eppendorf tube. The corresponding fragments were recovered with Agarose Gel Recovery Kit of MN (see Table 1), and the purity and concentration of the product were determined.

(14) The primers IRES-F and IRES-R were used to synthesize SEQ ID NO: 25 as templates. Using the system in Table 2, the conditions of PCR cycle were 98° C. 3 min, (98° C. 10 sec, 55° C. 15 sec, 72° C. 2 min)*35 cycle and 72° C.~10 min. The product was by agarose gel electrophoresis of 1.5%, and the fragment k of 605 bp was confirmed. The tapping gel was recovered in Eppendorf tube, and the corresponding fragments were recovered by agarose gel recovery kit of MN company (see Table 1), and the purity and concentration of the product were determined.

(15) The primers PDL1s1-F and PDL1s1-R were used to synthesize SEQ ID NO: 21 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment 1 of 754 bp was confirmed. The tapping gel was recovered in Eppendorf tube, and the corresponding fragments were recovered by agarose gel recovery kit of MN company (see Table 1), and the purity and concentration of the product were determined.

(16) The primers PDL1s2-F and PDL1s2-R were used to synthesize SEQ ID NO: 22 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment m of 777 bp was confirmed. The tapping gel was recovered in Eppendorf tube, and the corresponding fragments were recovered by agarose gel recovery kit of MN company (see Table 1), and the purity and concentration of the product were determined.

(17) The primers PDL1s3-F and PDL1s3-R were used to synthesize SEQ ID NO: 23 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment n of 774 bp was confirmed. The tapping gel was recovered in Eppendorf tube, and the corresponding fragments were recovered by agarose gel recovery kit of MN company (see Table 1), and the purity and concentration of the product were determined.

(18) The primers s0-F and s0-R were used to synthesize SEQ ID NO: 24 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment o of 729 bp was confirmed. The tapping gel was recovered in Eppendorf tube, and the corresponding fragments were recovered by agarose gel recovery kit of MN company (see Table 1), and the purity and concentration of the product were determined.

(19) The primers Fc-F and Fc-R were used to synthesize SEQ ID NO: 27 as templates. Using the system in Table 2, the conditions of PCR cycle were 98° C. 3 min, (98° C. 10 sec, 55° C. 15 sec, 72° C. 2 min)*35 cycle and 72° C. 10 min. The product was by agarose gel electrophoresis of 1.5%, and the fragment p of 726 bp was confirmed. The tapping gel was recovered in Eppendorf tube, and the corresponding fragments were recovered by agarose gel recovery kit of MN company (see Table 1), and the purity and concentration of the product were determined.

(20) DNA fragments (V2, k, 1, p), (V2, k, m, p), (V2, k, n, p), (V2, k, o, p) were added into the Eppendorf tube with a total volume of 5 μl and at a molar ratio of 1:1:1 respectively, and 15 μl homologous recombinant enzyme reaction solution. After evenly mixed, they were incubated at 42° C. for 30 minutes and transferred to ice for 2-3 minutes. The reaction solution was added to 50 μl TOP10 and rotated gently to evenly mix the content. Place the tube in ice for 30 minutes, and heatly shock the tube for 90 seconds in a constant temperature water bath pot preheated to 42° C., quickly transfer the tube to the ice bath, cool the cells for 2-3 minutes, add 900 μl LB culture medium to each tube, then transfer the tube to a shaking bed at 37° C., incubate for 1 hour to resuscitate the bacteria, take 100 μl transformed bacteria solution and coat it on Amp LB agar plate, invert the flat dish, and put it in a constant temperature incubator at 37° C., and culture for 16 hours. The correct clones were identified by colony PCR as recombinant lentivirus plasmids pCARmm-PDL1scFv1, pCARmm-PDL1scFv2, pCARmm-PDL1scFv3 and control pCARmm-scFv0. The correct clone would be identified with enzyme digestion (see FIGS. 6A-6H). 2. Packaging of 1vCARmm-PDL1scFv1, 1vCARmm-PDL1scFv2, 1vCARmm-PDL1scFv3, 1vCARmm-scFv0

(1) Complete medium: take out the pre-warmed fresh medium, add 10% FBS+5 ml Pen-Srep, and mix them upside down.

(2) 1×PBS solution: weigh 8 g of NaCl, 0.2 g of KCl, 3.58 g of $Na_2HPO_4.12H_2O$, 0.24 g of $KH_2PO4$, and put them in a 1000 ml beaker, and add 900 ml of Milli-Q grade ultrapure water to dissolve. After completion of the dissolution, the volume was adjusted to 1000 ml using a 1000 ml measuring cylinder, and the mixture was sterilized by heat sterilization at 121° C. for 20 minutes.

(3) 0.25% Trypsin solution: weigh 2.5 g of Trypsin, 0.19729 g EDTA, and put them in a 1000 ml beaker, and add 900 ml of 1×PBS solution to dissolve. After completion of the dissolution, the volume was adjusted to 1000 ml using a 1000 ml measuring cylinder, and the mixture was sterilized via 0.22 μM filter. It could be saved in the refrigerator at −20° C. for long-term use.

(4) 0.5M CaCl2 solution: weigh 36.75 g of $CaCl_2$), and dissolve it with 400 ml of Milli-Q grade ultrapure water; The volume was adjusted to 500 ml with Milli-Q grade ultrapure water, and mixed; The mixture was sterilized via 0.22 μM filter, and stored in 50 ml centrifuge tubes with about 45 ml in each tube at 4° C.

(5) 2×HBS solution: weigh 4.09 g of NaCl, 0.269 g of $Na_2HPO4$, 5.96 g of Hepes, and dissolve them with 400 ml Milli-Q grade ultrapure water; After calibrating the PH meter, the PH of the HBS solution was adjusted to 7.05 with 2M NaOH solution. It was about 3 ml of 2M NaOH to consume to adjust the PH of each bottle of HBS.

(6) The frozen HEK293T/17 cells were removed from the liquid nitrogen container and repidly transferred to a 37° C. water bath for 1-2 minutes, and then put them on a super clean bench. Aseptically transfer all the liquid in the freezing tube to a 10 $cm^2$ petri dish, and make up DMEM containing 10% FBS to 8 mL/10 $cm^2$ dish, and observe the cells under microscope after 24 hours. Passage was performed with the degree of cell confluence greater than 80%.

(7) HEK293T/17 cells with good cell status and no pollution were selected, and each 2-6 petri dishes were used as a group. After trypsinizing the cells, 4-12 ml of complete medium was pipetted with an electric pipette to add 2 ml to each digested dish to avoid drying the dish; All cells were isolated into single cell suspensions using a 1 ml pipette and transferred to medium bottles.

(8) The remaining cells in the above 2-6 petri dishes were transferred to the medium bottles, and the petri dishes were rinsed with the medium again.

(9) Close the cap of the medium bottles and turn them upside down for about 10 times to fully mixed the cell suspension. Transfer the cells to 8-24 10 $cm^2$ petri dishes. For each dish, there shall be about $4\times10^6$ cells/10 ml complete medium. If the cell density is significantly different from the expected, the number of cells is required to be counted, and then the cells will be inoculated according to the quantity of $4\times10^6$ per dish.

(10) Arrange each of the 6 petri dishes into a pile, and keep the fit between the upper and lower dishes. Shake the petri dishes left and right, back and forth several times to make cells fully spread out, and then put them into an incubator with 5% $CO_2$. The remaining cells were treated as the same.

(11) Upon Checking the passage cells, the cells shall be at 70-80% confluence, with full contour, good attachment and even distribution in petri dishes.

(12) For changing the solution, the medium was replaced with fresh complete medium with 9 ml per dish. The $CO_2$ concentration of incubator was increased to 8%.

(13) To prepare DNA/CaCl2 according to N+0.5. The amount of HEK293T/17 cell transfection plasmid per dish was used in the following ratios: recombinant lentiviral plasmid (20 μg), pPac-GP (15 μg), pPac-R (10 μg), pEnv-G (7.5 μg). Take a new 5 ml centrifuge tube, add 0.5M CaCl2: 0.25 ml, recombinant lentiviral plasmid 20 μg: pPac-GP 15 μg: pPac-R 10 μg: pEnv-G 7.5 μg, supplement ultrapure water to 0.5 ml, and cover the cap to mix them fully.

(14) Take another 5 ml centrifuge tube and add 0.5 ml DNA/CaCl2 solution. Open a vortex mixer, hold the upper end of the 5 ml centrifuge tube with one hand, and make the bottom of the tube contact the oscillation chamber, so that the liquid could spread on the tube wall. Take a 1 ml pipette with anther hand to suck 0.5 mL 2×HBS solution, add it into the centrifuge tube slowly and control the flow velocity. It was advisable to complete the drip in half a minute. After 2×HBS was added, it should be oscillated for another 5 seconds, and then stop oscillating. It could be directly added into the cells that need transfection.

(15) Take a dish of cells and drop 1 mL calcium transfection solution in the centrifuge tube in the dish to distribute the calcium transfection solution throughout the petri dish as much as possible;

(16) After the calcium transfection solution was added, the petri dish was marked on the cover, and put back in another incubator with 5% $CO_2$. Make sure that the petri dish was placed horizontally, and that there were no more than 6 petri dishes in each pile. These dishes were placed in the incubator with 5% $CO_2$ for 6-8 h.

(17) The $CO_2$ concentration of the first incubator was adjusted at 5%.

(18) The cells status was check 24 hours later. The cell confluence should be around 80-85% and in good condition. Aspirate the medium and replace 10 ml of fresh DMEM complete medium.

(19) The transfection efficiency was observed 48 hours later. Most cells were still adherent. It could be seen that more than 95% of the cells would have green fluorescence. The supernatant of the same virus packaging was collected together, and 10 mL of fresh medium was added to the petri dish.

(20) The same virus supernatant was collected again 72 hours later. The two collections were put together, and the petri dishes were discarded; the supernatant collected at this time contained the recombinant lentiviral vectors 1vCARmm-PDL1scFv1, 1vCARmm-PDL1scFv2, 1vCARmm-PDL1scFv3, 1vCARmm-scFv0.

Embodiment 2 Concentration and Detection of Recombinant Lentivirus Vector

Figure 7:
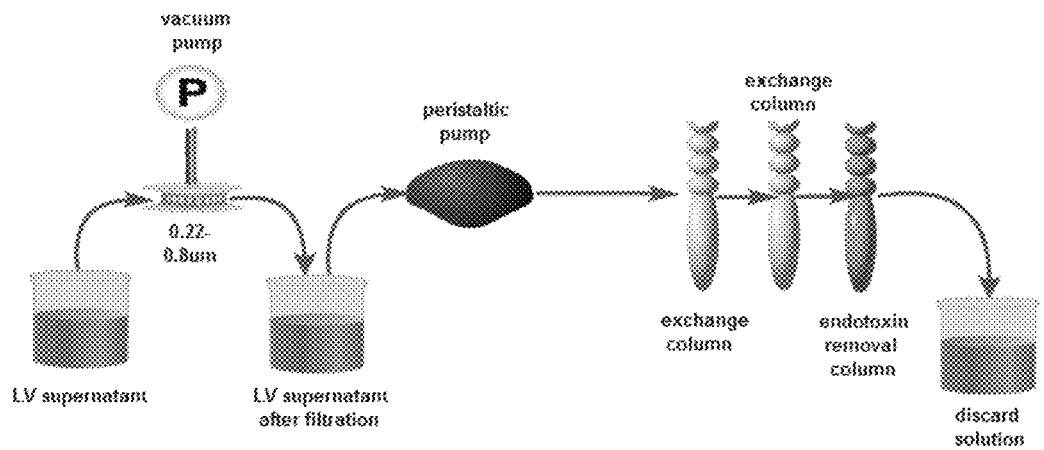
FIG. 7 is a flow chart of ion exchange chromatography for purification of recombinant lentivirus vector in embodiment 2 of the invention.

I. Purification of Recombinant Lentiviral Vectors by Ion Exchange Chromatography (See FIG. 7);

(1) The collected supernatant was filtered through a 0.22 μm-0.8 μm PES filter using a Thermo vacuum pump to remove impurities.

(2) 1.5M NaCl 250 mM Tris-HCl (PH6-8) was added to the supernatant at a ratio of 1:1 to 1:10

(3) Two ion exchange columns were placed in series, and they were passed through sequentially by 4 ml 1M NaOH, 4 ml 1M NaCl, 5 ml 0.15M NaCl 25 mM Tris-HCl (pH 6-8) solution.

(4) The solution obtained in step 2 was pumped into the ion exchange column with a peristaltic pump at a rate of 1-10 ml/min.

(5) After all the supernatant was passed through the column, it was washed with 10 ml of 0.15M NaCl 25 mM Tris-HCl (pH 6-8) solution.

(6) According to the sample size, 1-5 ml of 1.5M NaCl 25 mM Tris-HCl (pH 6-8) was used for elution and the eluate was collected.

(7) The eluate was divided into tubes about 25 to 50 μl each, and stored in a refrigerator with −80° C. for long-term storage.

II. Titre Determination (1) 293T cells were inoculated with 24-well plates. The number of cells in each well was $5 \times 10^4$, and the volume of medium added was 500 ul. As the growth rate of different types of cells was different, the rate of cell fusion during viral infection was 40%-60%.

(2) Three sterile EP tubes were prepared, and 90 ul fresh complete medium (high glucose DMEM+10% FBS) was added into each tube to inoculate the cells. 24 hours later, the cells in the two pores were taken and counted with a hemocytometer to determine the actual number of cells at the time of infection, denoted as N.

(3) 10 ul of the virus stock to be determined was added to the first tube. After gently mixing, 10 ul of the virus stock was added to the second tube, and then sequentially operated until the last tube; 410 ul complete medium (high glucose DMEM+10% FBS) was added into each tube, and the final volume was 500 ul.

(4) 20 hours after the infection, the cultural supernatant was removed and replaced with 500 μl complete medium (high glucose DMEM+10% FBS). The cells was continuously cultured for 48 hours in 5% $CO_2$.

(5) After 72 hours, the fluorescence expression was observed. Under normal circumstances, the number of fluorescence cells decreased with the increase of dilution ratio. At the same time, photos were taken.

(6) The cells were digested with 0.2 ml 0.25% trypsin-EDTA solution, and then they were placed at 37° C. for 1 minute. The whole cellular surface were purged with medium, and the cells were collected by centrifugation. Genomic DNA was extracted according to the instructions of DNeasy kit. 200 μl of eluent were added to each sample tube to remove DNA, and then they were quantified.

(7) The DNA detection qPCRmix manifold I was prepared (QPCR primer sequences were SEQ ID NO: 57-SEQ ID NO: 58):

| | |
|---|---|
| 2 × TaqMan Master Mix | 25 μl × n |
| Forward primer (100 pmol ml−1) | 0.1 μl × n |
| Reverse primer (100 pmol ml−1) | 0.1 μl × n |
| Probe (100 pmol ml−1) | 0.1 μl × n |
| $H_2O$ | 19.7 μl × n | n=number of reactions. For example, the total n were 40. 1 ml of 2× TaqMan Universal PCR Master Mix, 4 μl of forward primer, 4 μl of reverse primer, 4 μl of probe and 788 μl of $H_2O$ were mixed and Placed on ice after being shaken.

(8) The reference DNA detection qPCRmix manifold II were prepared (QPCR primer sequences were SEQ ID NO: 59-SEQ ID NO: 60):

| | |
|---|---|
| 2 × TaqMan Master Mix | 25 μl × n |
| 10 × RNaseP primer/probe mix | 2.5 μl × n |
| $H_2O$ | 17.5 μl × n | n=number of reactions. For example, the total n were 40. 1 ml of 2× TaqMan Universal PCR Master Mix, 100 μl pf 10× RNaseP primer/probe mix and 700 μl of $H_2O$ were mixed and placed on ice after being shaken.

(9) The PCR system was established on a pre-cooled 96-well PCR plate. Take 45 μl from each tube of manifold I to add to the wells of each row of A-D. Take 45 μl from each tube of manifold II to add to the wells of each row of E-G.

(10) 5 μl of the standard plasmid and the genomic DNA from the samples to be tested were taken respectively to add to the A-D row, and each sample was repeated once. 1 well was left to add 5 μl of water as no-template control.

(11) 5 μl of the genomic standards and the genomic DNA from the samples to be tested were taken respectively to add to the E-G row, and each sample was repeated once. 1 well was left to add 5 μl of water as no-template control.

(12) The quantitative PCR instrument used was the ABI PRISM 7500 quantitative system. The cyclic conditions were set to: 50° C. 2 min, 95° C. 10 min, (95° C. 15 sec, 60° C. 1 min)×40 cycle.

Data analysis: the copy number of lentiviral vectors integrated in the measured DNA samples was calibrated with the number of genomes to obtain the copy number of viruses integrated in each genome.

The calculation formula of integration units per ml (IU ml$^{-1}$) was as follows:

$$IU\ ml^{-1} = (C \times N \times D \times 1000)V$$

wherein: C=the average virus copy number per genome integration

N=number of cells at the time of infection (approximately $1 \times 10^5$)

D=dilution of the viral vector

V=the volume of diluted virus added

Figure 8:
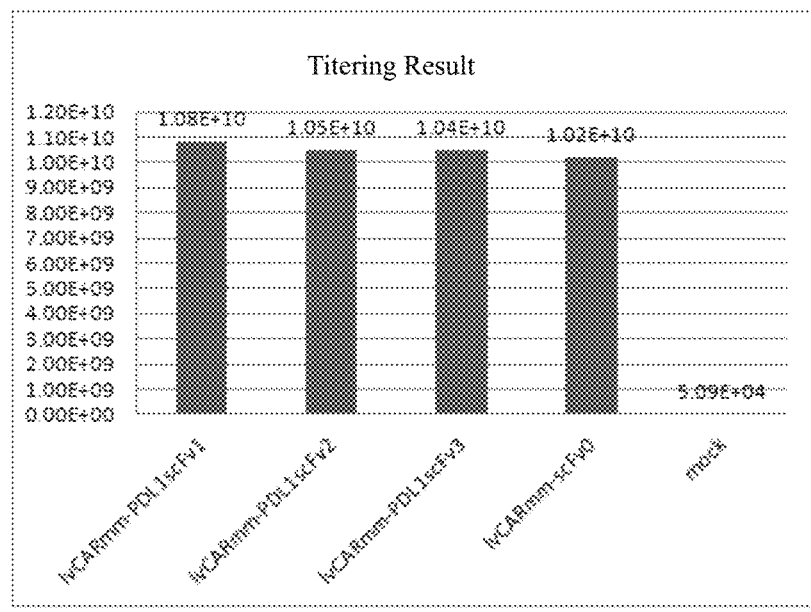
FIG. 8 is a schematic diagram of titer detection results of recombinant lentivirus vectors in embodiment 2 of the invention.

(13) Titer results of recombinant lentiviral vectors 1vCARmm-PDL1scFv1, 1vCARmm-PDL1scFv2, 1vCARmm-PDL1scFv3, 1vCARmm-scFv0 (see FIG. 8).

III. Endotoxin Determination (1) The working standard of endotoxin was 15EU per dose.

(2) Sensitivity of Tachypiens Amebocyte Lysate (TAL) λ=0.25EU/ml, 0.5 ml/tube.

(3) Dilution of endotoxin standard: take one endotoxin standard, dilute it into 4λ and 2λ solution with BET water, seal with sealing film and vortex for 15 min; During dilution, each dilution step should be mixed on the vertex mixer for 30s.

(4) Adding: Several TAL were taken, each was dissolved in 0.5 ml of BET water, and then divided into several exdotoxin-free tubes (0.1 ml each tube). Two of them were negative control which were added 0.1 ml of BET water to each of them.

Two tubes were positive control which were added 0.1 ml of endotoxin working standard solution with concentration of 2λ to each of them.

Two tubes were positive control of sample which were added 0.1 ml sample solution contained 2λ endotoxin standard (1 ml of 20× dilution of sample to be tested+1 ml of solution contained 4λ endotoxin standard=2 ml of 40× dilution of sample contained 2λ endotoxin standard).

Two tubes were positive control of sample which were added 0.1 ml sample solution contained 2λ endotoxin standard (1 ml of 20× dilution of sample to be tested+1 ml of solution contained 4λ endotoxin standard=2 ml of 40× dilution of sample contained 2λ endotoxin standard).

TABLE 5

Dilution ratio of exdotoxin and corresponding endotoxin content

| Dilution Multiple | Original Fluid | 5 | 10 | 20 | 40 | 80 | 160 |
|---|---|---|---|---|---|---|---|
| Corresponding EU/ml | 0.25 | 1.25 | 2.5 | 5 | 10 | 20 | 40 |
| Results | | | | | | | |

(5) The endotoxin detection results of the recombinant lentiviral vectors 1vCARmm-PDL1 scFv1, 1vCARmm-PDL1scFv2, 1vCARmm-PDL1scFv3, 1vCARmm-scFv0 (as shown in Table 6) showed that the endotoxin content was between 0-2.5 EU/ml, which met the requirements.

TABLE 6

Detection results of endotoxin of recombinant lentiviral vectors

| | Dilution Multiple | | | | | | |
|---|---|---|---|---|---|---|---|
| | Original Fluid | 5 | 10 | 20 | 40 | 80 | 160 |
| | Corresponding EU/ml | | | | | | |
| | 0.25 | 1.25 | 2.5 | 5 | 10 | 20 | 40 |
| lvCAR19-1761 | (+) | (+) | (−) | (−) | (−) | (−) | (−) |
| lvCAR19-1762 | (+) | (+) | (+) | (−) | (−) | (−) | (−) |
| lvCAR19-1763 | (+) | (+) | (−) | (−) | (−) | (−) | (−) |
| lvCAR19-1764 | (+) | (+) | (−) | (−) | (−) | (−) | (−) |
| lvCAR19-1765 | (−) | (−) | (−) | (−) | (−) | (−) | (−) |
| lvCAR19-1766 | (+) | (−) | (−) | (−) | (−) | (−) | (−) |
| lvCAR19-1767 | (+) | (+) | (−) | (−) | (−) | (−) | (−) |
| lvCAR19-1768 | (+) | (+) | (−) | (−) | (−) | (−) | (−) |
| lvCAR19-1769 | (+) | (+) | (+) | (−) | (−) | (−) | (−) |

IV. Measurement and Comparison of Mycoplasma.

(1) Three days before the experiment, the cell samples were cultured in antibiotic-free medium.

(2) 1 ml cell suspension (more than 1*105 cells) was collected and placed in a 1.5 ml centrifugal tube.

(3) Centrifuge for 1 min, collect sediment and discard culture medium.

(4) Adding 500 ul PBS, blowing or whirlpool oscillation with the gun head, and resuspend sediment. Centrifugation for 5 min at 13000×g.

(5) Repeat step (4).

(6) Add 50 μl Cell Lysis Buffer, blow and suck with gunhead, mix well, and incubate in water bath at 55° C. for 20 minutes.

(7) The samples were heated at 95° C. for 5 minutes.

(8) After centrifugation for 5 min, 5 μl supernatant was used as template. The 25 μl PCR reaction system was ddH20 6.5 μl, Myco Mix 2× Taq Plus Mix Master (Dye Plus) 12.5 μl and template 55 μl. The cycle conditions of PCR were 95° C. 30 sec, (95° C. 30 sec, 56° C. 30 sec, 72° C. 30 sec)*30 cycle and 72° C. 5 min.

(9) Mycoplasma detection results (as shown in FIG. 9) showed that recombinant lentiviral vectors 1vCARmm-PDL1scFv1, 1vCARmm-PDL1scFv2, 1vCARmm-PDL1scFv3 and 1vCARmm-scFv0 did not contain mycoplasma.

In embodiment 3, functional detection of recombinant lentiviral vectors 1vCARmm-PDL1scFv1, 1vCARmm-PDL1scFv2, 1vCARmm-PDL1scFv3 and 1vCARmm-scFv0.

I. Detection of Cellular Level Expression of CAR Gene:

(1) After infection of PBMC cells by recombinant lentiviral vectors 1vCARmm-PDL1scFv1, 1vCARmm-PDL1scFv2, 1vCARmm-PDL1scFv3 and 1vCARmm-scFv0, and control virus Mock. RT-PCR was used to detect the mRNA transcriptional levels of CAR gene and scFv gene by collecting cells, and to verify the expression of CAR gene and scFv gene. If the mRNA transcriptional level of CAR gene and scFv gene increased, the expression of transcription level was successful.

(2) After infection of PBMC cells by recombinant lentiviral vectors 1vCARmm-PDL1scFv1, 1vCARmm-PDL1scFv2, 1vCARmm-PDL1scFv3 and 1vCARmm-scFv0, and control virus Mock. western blot was used to detect the expression level of CAR protein by collecting cells, and to verify the expression of CAR gene. If the expression level of CAR protein increased, the translation level of CAR gene was successfully expressed.

(3) After infection of PBMC cells by recombinant lentiviral vectors 1vCARmm-PDL1scFv1, 1vCARmm-PDL1scFv2, 1vCARmm-PDL1scFv3 and 1vCARmm-scFv0, and control virus Mock. The expression level of scFv protein was detected by ELISA in the supernatant of cultured cells to verify the expression of scFv gene. If the expression level of scFv protein increased, the translation level of scFv gene was successfully expressed.

(4) Infect cells with 1vCARmm-PDL1scFv1, 1vCARmm-PDL1scFv2, 1vCARmm-PDL1scFv3 and 1vCARmm-scFv0 of MOI=15 and control virus Mock, after 48 hours, extract the total RNA and total protein of cells from the 6 hole plate to carry out the quantitative fluorescence PCR and immunoblot experiment respectively. Specific steps: wrapping four holes of 6-hole plate, adding corresponding PBS and RN to each hole, and staying overnight at 4° C. After 12 hours, the virus was coated with MOI=15 and placed in incubator at 37° C. for 5 hours. The virus supernatant in the 6 hole plate was discarded and washed twice with PBS. PBMC was coated with 1*106/hole (separated from human blood with lymphocyte separating fluid). Add 500 ul culture medium (containing 10% serum, 20 U/ml IL-2, Polybrene Bug/ml) and place static for 20 minutes, centrifuge for 30 minutes at 1000 g 20° C. and culture for 48 hours at 37° C.

(5) Total RNA was extracted from PBMC cells in 6 hole plate by Trizol method. Reverse transcription was used to amplify the cDNA. Quantitative fluorescence PCR experiment was performed with CAR gene QPCR primers (SEQ ID NO: 61-SEQ ID NO: 62) and scFv gene QPCR primers (SEQ ID NO: 67-SEQ ID NO: 68). The reaction system was shown in Table 7. The internal reference Actin was used as the control group to verify the transcription of the mRNA.

TABLE 7

| 20 μl qPCR reaction system | |
| --- | --- |
| reagent | volume(μl) |
| SYBR premix ex taq: | 10 μl |
| ROX Reverse Dye (50x) | 0.4 μl |
| upstream primers (2.5 μM): | 0.5 μl |
| downstream primers (2.5 μM): | 0.5 μl |
| cDNA | 1.0 μl |
| ddH$_2$O | 7.6 μl |

(6) Western Blot was used to separate the total proteins extracted from PBMC in accordance with relative molecular mass by polyacrylamide gel electrophoresis. The protein was transferred to PVDF membrane by wet rotation (4° C., 400 mA, 120 min). PVDF membranes were sealed at room temperature for 1 hour with a sealing solution (TBST solution containing 5% skimmed milk), and Biotinylated protein L was diluted at 1:1000 with the sealing solution. Then they were incubated with the sealed PVDF membranes at room temperature for overnight at 4° C. TBST was washed three times, 10 minutes each time. The corresponding SA-HRP was diluted at 1:500, and PVDF membrane was incubated at room temperature for 2 hours, and TBST was washed three times, 10 minutes each time. Amersham company's ECL+plus TM Western blotting system kit was used for color rendering. X-ray development produces film showing strips.

(7) Enzyme Linked ImmunoSorbent Assay (ELISA) was used to coat the 1:2, 1:5 and 1:10 diluted supernatant of cell culture into 96 hole plate. Negative control, positive control and blank hole were set up at the same time and overnight at 4° C. Wash three times the next day, add fresh 1:10000 diluted proteinG-HRP 0.1 ml to the reaction pore, incubate at 37° C. for 30-60 minutes, wash, and wash with pure water for the last time. The TMB substrate solution added into the reaction pore was 0.1 ml and incubated at 37° C. for 10-30 minutes. ELISA reaction termination solution added into each reaction pore was 0.05 ml. OD values of each pore were measured at 405 nm on the enzyme label.

Figure 10B:
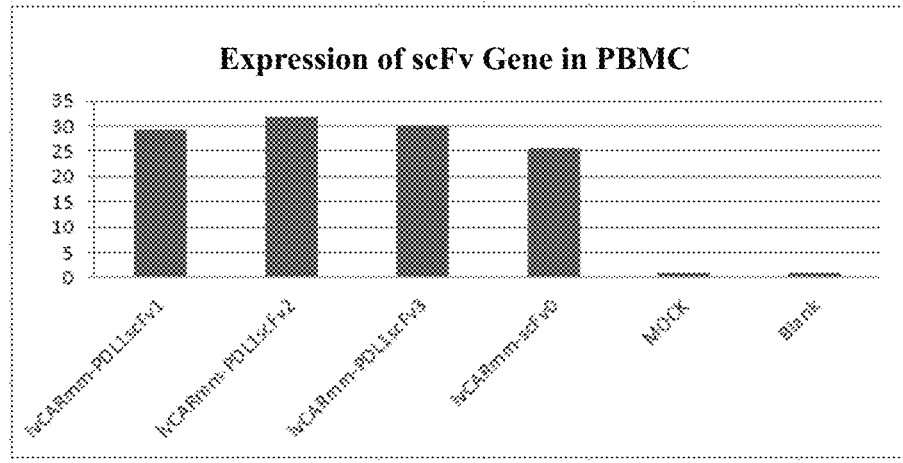

(8) RT-QPCR inspection showed that the transcription levels of CAR gene and scFv gene of recombinant lentivirus vector after infected with PBMC were significantly higher than those in empty cells (as shown in FIGS. 10A and 10B), indicating that the transcription levels of CAR gene and scFv gene were successfully expressed.

Figure 11A:
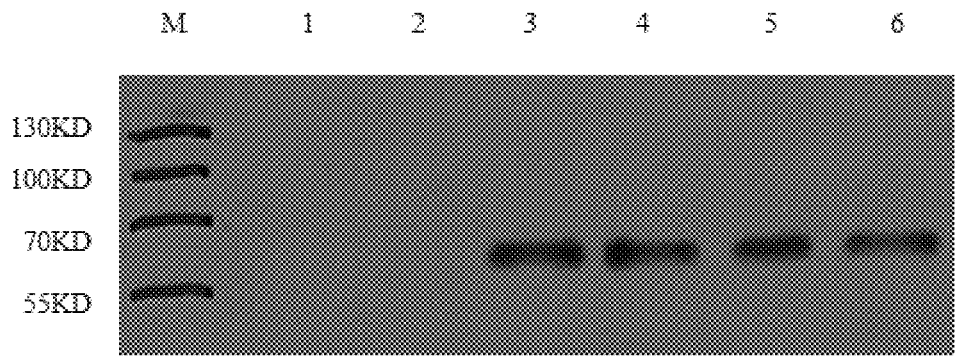
FIGS. 11A and 11B are WB detection diagrams of CAR protein expression in PBMC cells in embodiment 3 of the invention; where the results show that CAR protein is highly expressed in PBMC cells.
Figure 11B:
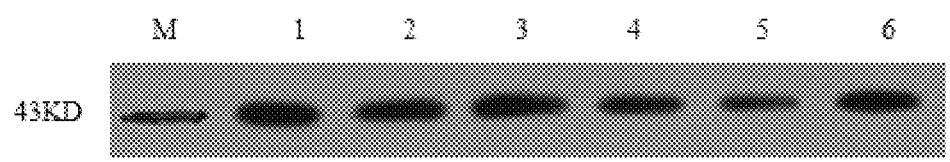

(9) Western Blot results showed that the expression level of CAR protein of recombinant lentivirus vector infected with PBMC was significantly higher than that of control virus MOCK and empty cells (as shown in FIGS. 11A and 11B), indicating that the translation level of CAR gene was successfully expressed.

Figure 12:
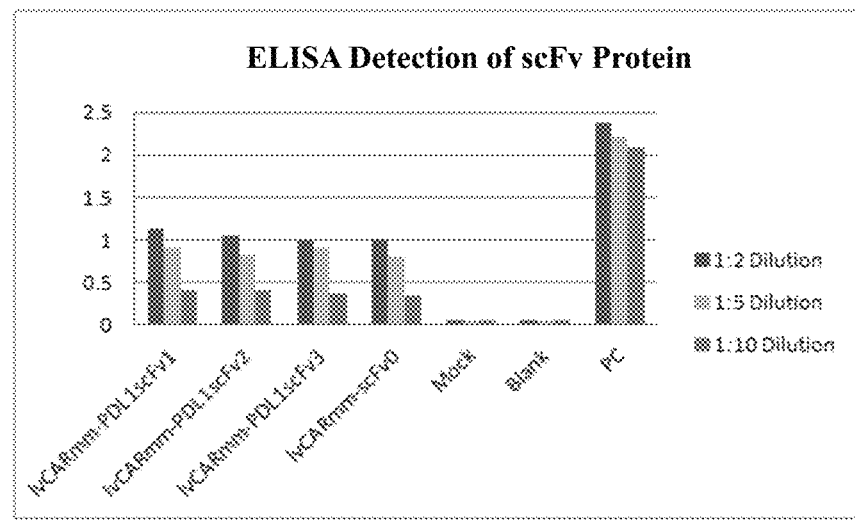
FIG. 12 is an ELISA test result of the expression of scFv protein in embodiment 3 of the invention. The results show that scFv protein is highly expressed in PBMC cells.

(10) Enzyme linked immunosorbent assay (ELISA) results showed that the expression level of scFv protein of recombinant lentivirus vector infected with PBMC was significantly higher than that of control virus MOCK and empty cells (as shown in FIG. 12), indicating that the translation level of scFv gene was successfully expressed.

II. Evaluation of Cytotoxicity Test.

(1) BCMA-K562 cells and PBMC cells were cultured respectively.

(2) Four days before the start of the experiment, culture virus infected PBMC cells of 1vCARmm-PDL1scFv1, 1vCARmm-PDL1scFv2, 1vCARmm-PDL1scFv3 and 1vCARmm-scFv0 of MOI=15 respectively for 72-96 h, then start to arrange the experiment.

(3) The target cells (BCMA-K562) 4×105 cells and effector cells (PBMC cells transduced by 1vCARmm-PDL1scFv1, 1vCARmm-PDL1scFv2, 1vCARmm-PDL1scFv3 and 1vCARmm-scFv0) 2.8×106 cells were collected. The cells were centrifuged at 800 g for 6 minutes and the supernatant was discarded.

(4) The target cells and effector cells were resuspended with 1 ml 1×PBS solution. The cells were centrifuged at 800 g for 6 minutes and the supernatant was discarded.

(5) Repeat step (3) for one time.

(6) 700 ul culture medium (1640 culture medium+10% FBS) was used to resuspend effector cells and 2 ml culture medium (1640 culture medium+10% FBS) was used to resuspend target cells.

(7) The experimental holes with effective target ratio of 1:1, 5:1 and 10:1 were set up, and the control group was set up with 3 compound holes in each group.

(8) 250×g, 5 min plate centrifugation.

(9) It was cultured in a 5% CO2 incubator at 37° C. for 24 hours.

(10) 250×g, 5 min plate centrifugation.

(11) The 50 ul supernatant of each hole was taken to the new 96 hole plate, and the 50 ul substrate solution was added to each hole (light avoidance operation).

(12) Breeding in dark for 25 minutes.

(13) 50 ul termination solution was added into each hole.

(14) 490 nm absorbance was measured by enzyme labeling.

(15) Average the three multiple holes; the average value of the absorbance values of all experimental holes, target cell holes and effector cell holes deducting the background absorbance values of the culture medium; the average value of the maximum absorbance values of target cells deducting the volume-corrected control absorbance values.

Figure 13:
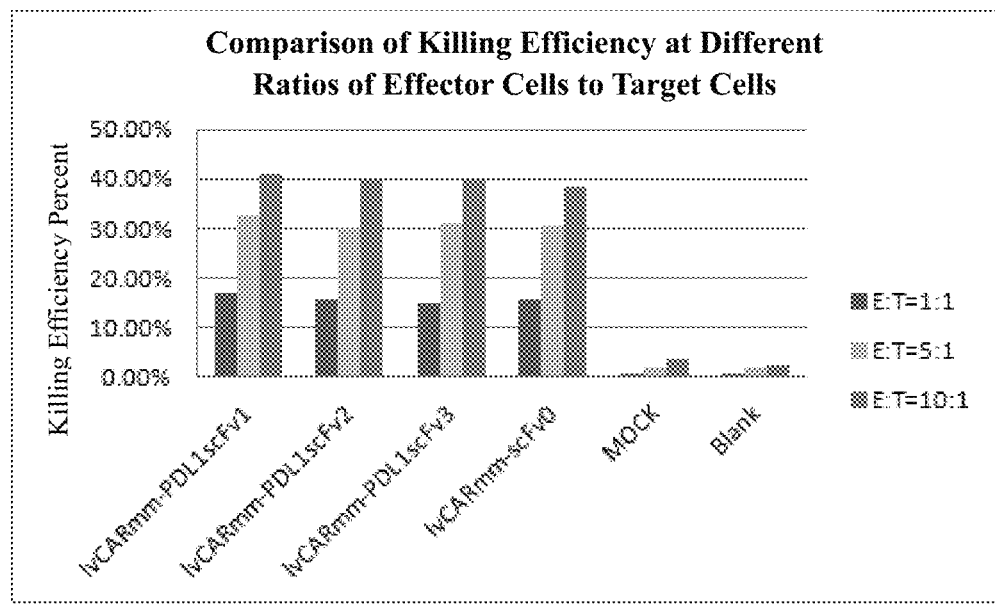
FIG. 13 is a schematic diagram of killing situation to the target cells after 24 h in co-culture of different effector cells with target cells in PBMC transduced by recombinant lentivirus vector of embodiment 3 of the invention.

(16) The corrected values obtained in step (15) are introduced into the following formula to calculate the percentage of cytotoxicity produced by each target-to-effect ratio. Results As shown in FIG. 13, the killing efficiency of PBMC cells transduced by 1vCARmm-PDL1scFv1, 1vCARmm-PDL1scFv2, 1vCARmm-PDL1scFv3 and 1vCARmm-scFv0 recombinant lentiviral vectors was significantly higher than that of PBMC empty cells and control viruses under several effect-target ratios, indicating that the expression of scFv gene had little effect on the function of CAR gene.

Killing efficiency=(experimental hole−effector cell hole−target cell hole)/(maximum hole of target cell−target cell hole)×100%

III. Evaluation of Blocking Effect of PDL1 (mRNA Transcription Level of PD1, IL2, TNFα and IFNγ).

(1) Culture BCMA-PDL1-K562 cells and PBMC cells respectively.

(2) Four days before the start of the experiment, culture virus infected PBMC cells of 1vCARmm-PDL1scFv1, 1vCARmm-PDL1scFv2, 1vCARmm-PDL1scFv3 and 1vCARmm-scFv0 of MOI=15 respectively for 72-96 h, then start to arrange the experiment.

(3) The target cells (BCMA-PDL1-K562) $4 \times 10^5$ cells and effector cells (PBMC cells transduced by 1vCARmm-PDL1scFv1, 1vCARmm-PDL1scFv2, 1vCARmm-PDL1scFv3 and 1vCARmm-scFv0) $2.8 \times 10^6$ cells were collected. The cells were centrifuged at 800 g for 6 minutes and the supernatant was discarded.

(4) The target cells and effector cells were resuspended with 1 ml 1×PBS solution. The cells were centrifuged at 800 g for 6 minutes and the supernatant was discarded.

(5) Repeat step (4) for one time.

(6) 700 ul culture medium (1640 culture medium+10% FBS) was used to resuspend effector cells and 2 ml culture medium (1640 culture medium+10% FBS) was used to resuspend target cells.

(7) The experimental holes with effective target ratio of 10:1 were set up, and the control group was set up.

(8) 250×g, 5 min plate centrifugation.

(9) Cultured in 5% CO2 incubator at 37° C. for 24 hours, centrifuged at 1000×g for 2 minutes, and the total mRNA was collected. The mRNA transcription levels of PD1, IL2, TNFα and IFNγ were detected by reversing cDNA.

(10) Quantitative fluorescence PCR experiment was performed with PD1 gene QPCR primers (SEQ ID NO: 63-SEQ ID NO: 64), IL2 gene QPCR primers (SEQ ID NO: 65-SEQ ID NO: 66), TNFα gene QPCR primers (SEQ ID NO: 69-SEQ ID NO: 70) and IFNγ gene QPCR primers (SEQ ID NO: 71-SEQ ID NO: 72). The reaction system was shown in Table 6. The internal reference Actin was used as the control group to verify the transcription of the mRNA.

Figure 14:
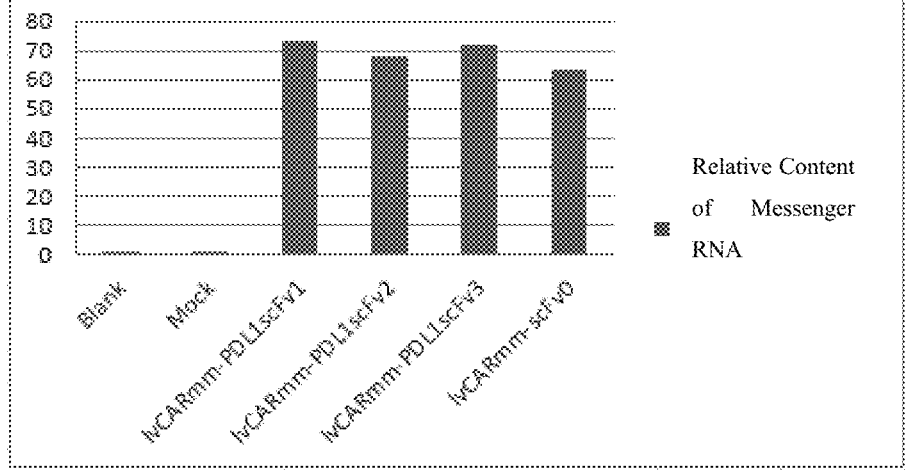
FIG. 14 is a schematic diagram of the change of PD1 mRNA transcription level after 24 h in co-culture of different effector cells with target cells in embodiment 3 of the invention.
Figure 15A:
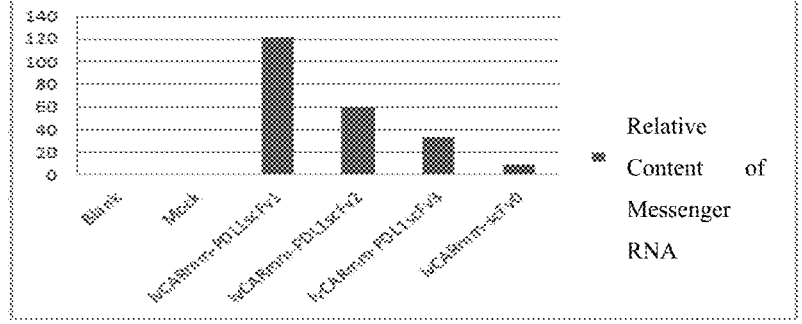
FIGS. 15A-15C are schematic diagrams of 24-hour cytokine transcription level under co-culture conditions of different effector cells and target cells in embodiment 3 of the invention, where
Figure 15B:
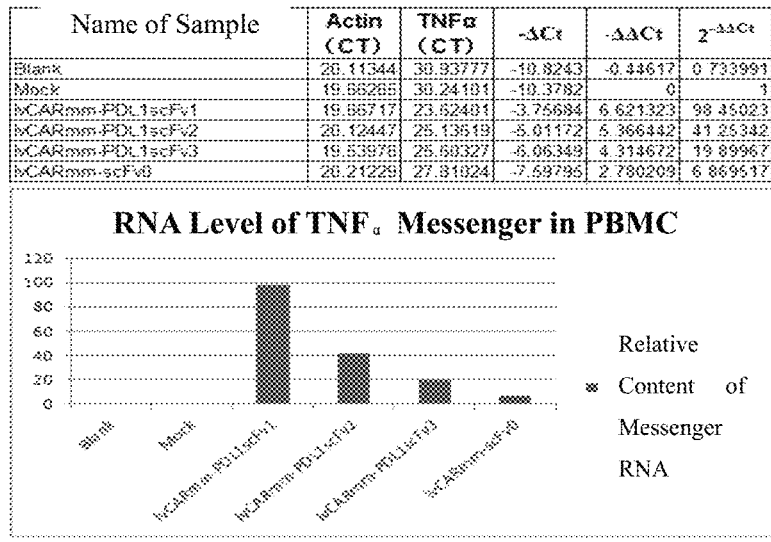
Figure 15C:
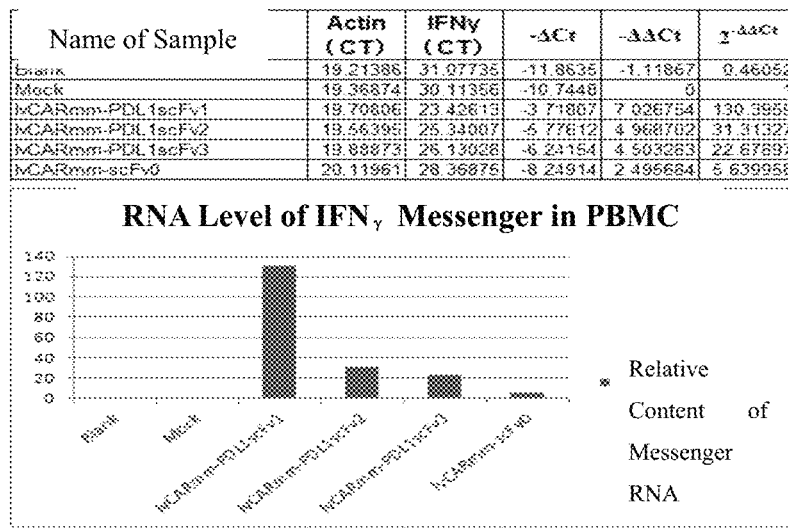

(11) RT-QPCR results showed that after incubation of PBMC transduced by 1vCARmm-PDL1scFv1, 1vCARmm-PDL1scFv2, 1vCARmm-PDL1scFv3 and 1vCARmm-scFv0 and target cells, mRNA level of PD1 gene is significantly increased compared with Mock group and empty cell group, but mRNA level of PD1 gene has no big difference among 1vCARmm-PDL1scFv1, 1vCARmm-PDL1scFv2, 1vCARmm-PDL1scFv3 and 1vCARmm-scFv0 (as shown in FIG. 14), which indicates the PD1 expression level of T cell has simultaneously improved after being activated. Later, it is been found that the mRNA transcription level of IL2, TNFα and IFNγ of 1vCARmm-PDL1scFv1, 1vCARmm-PDL1scFv2 and 1vCARmm-PDL1scFv3 is significantly improved than that of control virus 1vCARmm-scFv0 by inspecting the mRNA transcription level of IL2, TNFα and IFNγ, where the mRNA transcription level of IL2, TNFα and IFNγ is most obvious in the group of 1vCARmm-PDL1scFv1 (as shown in FIGS. 15A-15C). The higher expression level of gene of IL2, TNFα and IFNγ is, the T cell is more activated, which indicate 1vCARmm-PDL1scFv1 can effectively block the PD1/PDL1 signaling pathway, relieve the inhibition effect of T cell activating related genes, block the PD1/PDL1 signaling pathway in vivo in future to inhibit immune escape and improve the efficacy of CAR-T cell therapy for solid tumors.

What is claimed is:

1. A PDL1 block CAR-T transgenic vector for suppressing immune escape, comprising:

AmpR sequence containing ampicillin resistance gene for amplifying target bacterial strains by a large number, having the sequence of SEQ ID NO: 1;

prokaryotic replicon pUC Ori sequence for plasmid replication, having the sequence of SEQ ID NO: 2;

SV40 Ori sequence of viral replicator for enhancing replication in eukaryotic cells, having the sequence of SEQ ID NO: 3;

eWPRE enhanced posttranscriptional regulatory element of Groundhog hepatitis B virus for enhancing an expression efficiency of transgene, having the sequence of SEQ ID NO: 11;

human EF1 alpha promoter for eukaryotic transcription of chimeric antigen receptor genes, having the sequence of SEQ ID NO: 12;

lentivirus packaging cis-elements for lentivirus packaging;

a nucleotide sequence encoding a humanized single chain antibody fragment of human PDL1; and the humanized single chain antibody fragment of the human PDL1 is PDL1scFv1 encoded by the sequence of SEQ ID NO: 21, or PDL1scFv2 encoded by the sequence of SEQ ID NO: 22, or PDL1 scFv3 encoded by the sequence of SEQ ID NO: 23;

IRES ribosome binding sequence for co-transcription and expression of proteins, having the sequence of SEQ ID NO: 25;

a nucleotide sequence encoding IL6 signal peptide, wherein the nucleotide sequence is shown in SEQ ID NO: 26;

a nucleotide sequence encoding a human antibody Fc segment, wherein the nucleotide sequence is shown in SEQ ID NO: 27; and a nucleotide sequence encoding chimeric antigen receptors of a second-generation CAR or a third-generation CAR for integrating recognition, transmission and initiation.

2. The PDL1 block CAR-T transgenic vector according to claim 1, wherein the lentivirus packaging cis-element is a second-generation lentivirus vector, and the second-generation lentivirus vector comprises: lentivirus 5 terminal LTR having the sequence of SEQ ID NO: 5, lentivirus 3 terminal self-Inactivating LTR having the sequence of SEQ ID NO: 6, Gag cis-element having the sequence of SEQ ID NO: 7, RRE cis-element having the sequence of SEQ ID NO: 8, env cis-element having the sequence of SEQ ID NO: 9, and cPPT cis-elements having the sequence of SEQ ID NO: 10.

3. The PDL1 block CAR-T transgenic vector according to claim 2, wherein the eWPRE enhanced posttranscriptional regulatory element of groundhog hepatitis B virus has six nucleotide enhanced mutations, including g.396G >A, g.397C >T, g.398T >C, g.399G >A, g.400A >T and g.411A >T.

4. The PDL1 block CAR-T transgenic vector according to claim 1, wherein the lentivirus packaging cis-element-is a third-generation lentivirus vector, and the third-generation generation lentivirus vector comprises: lentivirus 5 terminal LTR having the sequence of SEQ ID NO: 5, lentivirus 3 terminal self-Inactivating LTR having the sequence of SEQ ID NO: 6, Gag cis-element having the sequence of SEQ ID NO: 7, RRE cis-element having the sequence of SEQ ID NO: 8, env cis-element having the sequence of SEQ ID NO: 9, cPPT cis-elements having the sequence of SEQ ID NO: 10, and RSV promoter having the sequence of SEQ ID NO: 4.

5. The PDL1 block CAR-T transgenic vector according to claim 4, wherein the eWPRE enhanced posttranscriptional regulatory element of groundhog hepatitis B virus has six nucleotide enhanced mutations, including g.396G >A, g.397C >T, g.398T >C, g.399G >A, g.400A >T and g.411A >T.

6. The PDL1 block CAR-T transgenic vector according to claim 1, wherein the chimeric antigen receptors of the second-generation CAR comprises: CD8 leader chimeric receptor signal peptide encoded by the sequence of SEQ ID NO: 13, BCMA single chain antibody fragment light chain VL encoded by the sequence of SEQ ID NO: 14, Optimal Linker C encoded by the sequence of SEQ ID NO: 15, BCMA single chain antibody fragment heavy chain VH encoded by the sequence of SEQ ID NO: 16, CD8 Hinge chimeric receptor hinges encoded by the sequence of SEQ ID NO: 17, CD8 Transmembrane chimeric receptor transmembrane regions encoded by the sequence of SEQ ID NO: 18, CD137 chimeric receptor costimulatory factors encoded by the sequence of SEQ ID NO: 19, and TCR chimeric receptor T cell activation domains encoded by the sequence of SEQ ID NO: 20;
the chimeric antigen receptors of the third-generation CAR comprises: CD8 leader chimeric receptor signal peptide encoded by the sequence of SEQ ID NO: 13, BCMA single chain antibody fragment light chain VL encoded by the sequence of SEQ ID NO: 14, Optimal Linker C encoded by the sequence of SEQ ID NO: 15, BCMA single chain antibody fragment heavy chain VH encoded by the sequence of SEQ ID NO: 16, CD8 Hinge chimeric receptor hinges encoded by the sequence of SEQ ID NO: 17, CD8 Transmembrane chimeric receptor transmembrane regions encoded by the sequence of SEQ ID NO: 18, CD137 chimeric receptor costimulatory factors encoded by the sequence of SEQ ID NO: 19, TCR chimeric receptor T cell activation domains encoded by the sequence of SEQ ID NO: 20, and CD28 chimeric receptor costimulatory factors encoded by the sequence of SEQ ID NO: 28.

7. The PDL1 block CAR-T transgenic vector according to claim 6, wherein the eWPRE enhanced posttranscriptional regulatory element of groundhog hepatitis B virus has six nucleotide enhanced mutations, including g.396G >A, g.397C >T, g. 398T >C, g.399G >A, g.400A >T and g.411A >T.

8. The PDL1 block CAR-T transgenic vector according to claim 1, wherein the eWPRE enhanced posttranscriptional regulatory element of groundhog hepatitis B virus has six nucleotide enhanced mutations, including g.396G>A, g.397C>T, g.398T>C, g.399G>A, g.400A>T and g.411A>T.

9. A preparation method of the PDL1 block CAR-T transgenic vector of claim 1, comprising the following steps:
(1) storing the AmpR sequence containing ampicillin resistance gene having the sequence of SEQ ID NO: 1, the prokaryotic replicon pUC Ori sequence having the sequence of SEQ ID NO: 2, the virus replicon SV40 Ori sequence having the sequence of SEQ ID NO: 3, the lentivirus packaging cis-element for lentivirus packaging, and the eWPRE enhanced posttranscriptional regulatory element of hepatitis B virus having the sequence of SEQ ID NO: 11 on a lentivirus skeleton plasmid;
(2) combining the human EF1αpromoter having the sequence of SEQ ID NO: 12 and the chimeric antigen receptors of the second-generation CAR or third-generation CAR for integrating recognition, transmission and initiation to form a second-generation CAR design scheme or a third-generation CAR design scheme; and cloning the second-generation CAR design scheme or the third-generation CAR design scheme into lentivirus skeleton plasmids by enzymatic digestion, ligation and recombination reaction to obtain recombinant lentivirus plasmids designed by the second-generation CAR or the third-generation CAR;
(3) cloning the nucleotide sequence encoding humanized single-chain antibodies fragment PDL1 scFv1, PDL1 scFv2, or PDL1 scFv3 of human PDL1, the IRES ribosome binding sequence, the nucleotide sequence encoding IL6 signal peptide and the nucleotide sequence encoding human antibody Fc fragment into recombinant lentiviral plasmids respectively to obtain PDL1 recombinant lentiviral plasmids pCARmm-PDL1scFv1, pCARmm-PDL1scFv2, or pCARmm-PDL1 scFv3;
(4) transfecting the PDL1 recombinant lentiviral plasmids pCARmm-PDL1scFv1, pCARmm-PDL1scFv2, or pCARmm-PDL1scFv3 into HEK293T/17 cells with lentiviral packaging plasmids pPac-GP, pPac-R and membrane protein pEnv-G respectively; wherein after gene transcription is completed in HEK293T/17 cells, recombinant lentiviral vectors are successfully packaged and released into a supernatant of a HEK293T/17 cells culture medium; and then collecting the supernatant containing the recombinant lentiviral vectors; and
(5) purifying supernatant containing the recombinant lentiviral vectors by column purification with filtration, adsorption and elution to obtain the recombinant lentivirus vectors respectively.

10. The preparation method according to claim 9, wherein in step (3), whole CAR gene expression is initiated by human EF1αa promoter; CAR protein is located on a surface of cell membrane, recognizes BCMA antigen, stimulates T cell proliferation and cytokine secretion, and activates an expression of downstream signaling pathway; when scFv region binds to BCMA antigen, a signal is transmitted to the cell through chimeric receptor, producing a series of biological effects including proliferation of T-cells, secretion of cytokines, secretion of anti-apoptotic proteins, delayed cell death, and lysis of target cells; a fusion protein of PDL1 scFv and Fc is co-expressed by IRES ribosome binding sequence, and is secreted outside the cell under a guidance of IL6 signal peptide; through a binding of the fusion protein with PDL1, a binding of PD1 and PDL1 is blocked, and a signal path of PD1/PDL1 is blocked, to achieve an effect of suppressing immune escape.

11. The preparation method according to claim 9, wherein in step (5), the step of the filtration comprises: controlling a volume of the supernatant from 200 ml to 2000 ml, a vacuum degree from -0.5 MPA to 0.9 MPA to prevent a loss of vectors caused by blockage; step of the adsorption comprises: controlling a PH value of solution from 6 to 8, and preventing the recombinant lentiviral vector from inactivating due to a change of PH; and the step of the elution comprises: controlling an ionic strength of eluent at 0.5 M-1.0 M, and preventing a change of the ionic strength leading to incomplete elution or vector deactivation.

12. The preparation method according to claim 9, wherein the lentivirus packaging cis-element is a second-generation lentivirus vector, and the second-generation lentivirus vector comprises: lentivirus 5 terminal LTR having the sequence of SEQ ID NO: 5, lentivirus 3 terminal self-Inactivating LTR having the sequence of SEQ ID NO: 6, Gag cis-element having the sequence of SEQ ID NO: 7, RRE cis-element having the sequence of SEQ ID NO: 8, env cis-element having the sequence of SEQ ID NO: 9, and cPPT cis-elements having the sequence of SEQ ID NO: 10.

13. The preparation method according to claim 12, wherein in step (3), whole CAR gene expression is initiated by human EF1αpromoter; CAR protein is located on a surface of cell membrane, recognizes BCMA antigen, stimulates T cell proliferation and cytokine secretion, and activates an expression of downstream signaling pathway; when scFv region binds to BCMA antigen, a signal is transmitted to the cell through chimeric receptor, producing a series of biological effects including proliferation of T-cells, secretion of cytokines, secretion of anti-apoptotic proteins, delayed cell death, and lysis of target cells; a fusion protein of PDL1scFv and Fc is co-expressed by IRES ribosome binding sequence, and is secreted outside the cell under a guidance of IL6 signal peptide; through a binding of the fusion protein with PDL1, a binding of PD1 and PDL1 is blocked, and a signal path of PD1/PDL1 is blocked, to achieve an effect of suppressing immune escape.

14. The preparation method according to claim 12, wherein in step (5), the step of the filtration comprises: controlling a volume of the supernatant from 200 ml to 2000 ml, a vacuum degree from 0.5 MPA to 0.9 MPA to prevent a loss of vectors caused by blockage; step of the adsorption comprises: controlling a PH value of solution from 6 to 8, and preventing the recombinant lentiviral vector from inactivating due to a change of PH; and the step of the elution comprises: controlling an ionic strength of eluent at 0.5 M-1.0 M, and preventing a change of the ionic strength leading to incomplete elution or vector deactivation.

15. The preparation method according to claim 9, wherein the lentivirus packaging cis-element is a third-generation lentivirus vector, and the third-generation lentivirus vector comprises: lentivirus 5 terminal LTR having the sequence of SEQ ID NO: 5, lentivirus 3 terminal self-Inactivating LTR having the sequence of SEQ ID NO: 6, Gag cis-element having the sequence of SEQ ID NO: 7, RRE cis-element having the sequence of SEQ ID NO: 8, env cis-element having the sequence of SEQ ID NO: 9, cPPT cis-elements having the sequence of SEQ ID NO: 10, and RSV promoter having the sequence of SEQ ID NO: 4.

16. The preparation method according to claim 15, wherein in step (3), whole CAR gene expression is initiated by human EF1αpromoter; CAR protein is located on a surface of cell membrane, recognizes BCMA antigen, stimulates T cell proliferation and cytokine secretion, and activates an expression of downstream signaling pathway; when scFv region binds to BCMA antigen, a signal is transmitted to the cell through chimeric receptor, producing a series of biological effects including proliferation of T-cells, secretion of cytokines, secretion of anti-apoptotic proteins, delayed cell death, and lysis of target cells; a fusion protein of PDL1 scFv and Fc is co-expressed by IRES ribosome binding sequence, and is secreted outside the cell under a guidance of IL6 signal peptide; through a binding of the fusion protein with PDL1, a binding of PD1 and PDL1 is blocked, and a signal path of PD1/PDL1 is blocked, to achieve an effect of suppressing immune escape.

17. The preparation method according to claim 9, wherein the chimeric antigen receptors of the second-generation CAR comprises: CD8 leader chimeric receptor signal peptide encoded by the sequence of SEQ ID NO: 13, BCMA single chain antibody fragment light chain VL encoded by the sequence of SEQ ID NO: 14, Optimal Linker C encoded by the sequence of SEQ ID NO: 15, BCMA single chain antibody fragment heavy chain VH encoded by the sequence of SEQ ID NO: 16, CD8 Hinge chimeric receptor hinges encoded by the sequence of SEQ ID NO: 17, CD8 Transmembrane chimeric receptor transmembrane regions encoded by the sequence of SEQ ID NO: 18, CD137 chimeric receptor costimulatory factors encoded by the sequence of SEQ ID NO: 19, and TCR chimeric receptor T cell activation domains encoded by the sequence of SEQ ID NO: 20;

the chimeric antigen receptors of the third-generation CAR comprises: CD8 leader chimeric receptor signal peptide encoded by the sequence of SEQ ID NO: 13, BCMA single chain antibody fragment light chain VL encoded by the sequence of SEQ ID NO: 14, Optimal Linker C encoded by the sequence of SEQ ID NO: 15, BCMA single chain antibody fragment heavy chain VH encoded by the sequence of SEQ ID NO: 16, CD8 Hinge chimeric receptor hinges encoded by the sequence of SEQ ID NO: 17, CD8 Transmembrane chimeric receptor transmembrane regions encoded by the sequence of SEQ ID NO: 18, CD137 chimeric receptor costimulatory factors encoded by the sequence of SEQ ID NO: 19, TCR chimeric receptor T cell activation domains encoded by the sequence of SEQ ID NO: 20, and CD28 chimeric receptor costimulatory factors encoded by the sequence of SEQ ID NO: 28.

18. The preparation method according to claim 17, wherein in step (3), whole CAR gene expression is initiated by human EF1αpromoter; CAR protein is located on a surface of cell membrane, recognizes BCMA antigen, stimulates T cell proliferation and cytokine secretion, and activates an expression of downstream signaling pathway; when scFv region binds to BCMA antigen, a signal is transmitted to the cell through chimeric receptor, producing a series of biological effects including proliferation of T-cells, secretion of cytokines, secretion of anti-apoptotic proteins, delayed cell death, and lysis of target cells; a fusion protein of PDL1scFv and Fc is co-expressed by IRES ribosome binding sequence, and is secreted outside the cell under a guidance of IL6 signal peptide; through a binding of the fusion protein with PDL1, a binding of PD1 and PDL1 is blocked, and a signal path of PD1/PDL1 is blocked, to achieve an effect of suppressing immune escape.

19. The preparation method according to claim 9, wherein the eWPRE enhanced posttranscriptional regulatory element of groundhog hepatitis B virus has six nucleotide enhanced mutations, including g.396G >A, g.397C >T, g.398T >C, g.399G >A, g.400A >T and g.411A >T.

20. The preparation method according to claim 19, wherein in step (3), whole CAR gene expression is initiated by human EF1αpromoter; CAR protein is located on a surface of cell membrane, recognizes BCMA antigen, stimulates T cell proliferation and cytokine secretion, and activates an expression of downstream signaling pathway; when scFv region binds to BCMA antigen, a signal is transmitted to the cell through chimeric receptor, producing a series of biological effects including proliferation of T-cells, secretion of cytokines, secretion of anti-apoptotic proteins, delayed cell death, and lysis of target cells; a fusion protein of PDL1scFv and Fc is co-expressed by IRES ribosome binding sequence, and is secreted outside the cell under a guidance of IL6 signal peptide; through a binding of the fusion protein with PDL1, a binding of PD1 and PDL1 is blocked, and a signal path of PD1/PDL1 is blocked, to achieve an effect of suppressing immune escape.

* * * * *

SEQUENCE LISTING

<160> NUMBER OF SEQ ID NOS: 72

<210> SEQ ID NO 1
<211> LENGTH: 861
<212> TYPE: DNA
<213> ORGANISM: Artificial sequence
<220> FEATURE:
<223> OTHER INFORMATION: the sequence is synthetized

<400> SEQUENCE: 1

```
atgagtattc aacatttccg tgtcgccctt attcccttt ttgcggcatt ttgccttcct      60 gttttttgctc acccagaaac gctggtgaaa gtaaaagatg ctgaagatca gttgggtgca     120
cgagtgggtt acatcgaact ggatctcaac agcggtaaga tccttgagag ttttcgcccc     180
gaagaacgtt ttccaatgat gagcactttt aaagttctgc tatgtggcgc ggtattatcc     240
cgtattgacg ccgggcaaga gcaactcggt cgccgcatac actattctca gaatgacttg     300
gttgagtact caccagtcac agaaaagcat cttacggatg gcatgacagt aagagaatta     360
tgcagtgctg ccataaccat gagtgataac actgcggcca acttacttct gacaacgatc     420
ggaggaccga aggagctaac cgcttttttg cacaacatgg gggatcatgt aactcgcctt     480
gatcgttggg aaccggagct gaatgaagcc ataccaaacg acgagcgtga ccacgatg      540 cctgtagcaa tggcaacaac gttgcgcaaa ctattaactg gcgaactact tactctagct     600
tcccggcaac aattaataga ctggatggag gcggataaag ttgcaggacc acttctgcgc     660
tcggcccttc cggctggctg gtttattgct gataaatctg gagccggtga gcgtgggtct     720
cgcggtatca ttgcagcact ggggccagat ggtaagccct cccgtatcgt agttatctac     780
acgacgggga gtcaggcaac tatggatgaa cgaaatagac agatcgctga gataggtgcc     840
tcactgatta agcattggta a                                              861
```

<210> SEQ ID NO 2
<211> LENGTH: 674
<212> TYPE: DNA
<213> ORGANISM: Artificial sequence
<220> FEATURE:
<223> OTHER INFORMATION: the sequence is synthetized

<400> SEQUENCE: 2

```
cccgtagaaa agatcaaagg atcttcttga gatccttttt ttctgcgcgt aatctgctgc      60
ttgcaaacaa aaaaaccacc gctaccagcg gtggtttgtt tgccggatca agagctacca     120
actctttttc cgaaggtaac tggcttcagc agagcgcaga taccaaatac tgtccttcta     180
gtgtagccgt agttaggcca ccacttcaag aactctgtag caccgcctac atacctcgct     240
ctgctaatcc tgttaccagt ggctgctgcc agtggcgata gtcgtgtct taccgggttg      300
gactcaagac gatagttacc ggataaggcg cagcggtcgg gctgaacggg gggttcgtgc     360
acacagccca gcttggagcg aacgacctac accgaactga gatacctaca gcgtgagcta    420
tgagaaagcg ccacgcttcc cgaagggaga aaggcggaca ggtatccggt aagcggcagg    480
gtcggaacag gagagcgcac gagggagctt ccagggggaa acgcctggta tctttatagt     540
cctgtcgggt ttcgccacct ctgacttgag cgtcgatttt tgtgatgctc gtcaggggggg    600
cggagcctat ggaaaaacgc cagcaacgcg gccttttac ggttcctggc cttttgctgg     660
ccttttgctc acat                                                       674
```

<210> SEQ ID NO 3
<211> LENGTH: 147
<212> TYPE: DNA
<213> ORGANISM: Artificial sequence
<220> FEATURE:
<223> OTHER INFORMATION: the sequence is synthetized

<400> SEQUENCE: 3

```
atcccgcccc taactccgcc cagttccgcc cattctccgc cccatggctg actaatttt      60
tttatttatg cagaggccga ggccgcctcg gcctctgagc tattccagaa gtagtgagga    120
ggcttttttg gaggcctaga cttttgc                                         147
```

<210> SEQ ID NO 4
<211> LENGTH: 228
<212> TYPE: DNA
<213> ORGANISM: Artificial sequence
<220> FEATURE:
<223> OTHER INFORMATION: the sequence is synthetized

<400> SEQUENCE: 4

```
gtagtcttat gcaatactct tgtagtcttg caacatggta acgatgagtt agcaacatgc      60
cttacaagga gagaaaaagc accgtgcatg ccgattggtg gaagtaaggt ggtacgatcg     120
tgccttatta ggaaggcaac agacgggtct gacatggatt ggacgaacca ctgaattgcc    180
gcattgcaga gatattgtat ttaagtgcct agctcgatac aataaacg                  228
```

<210> SEQ ID NO 5
<211> LENGTH: 180
<212> TYPE: DNA
<213> ORGANISM: Artificial sequence
<220> FEATURE:
<223> OTHER INFORMATION: the sequence is synthetized

<400> SEQUENCE: 5
ggtctctctg gttagaccag atctgagcct gggagctctc tggctaacta gggaacccac    60
tgcttaagcc tcaataaagc ttgccttgag tgcttcaagt agtgtgtgcc cgtctgttgt   120
gtgactctgg taactagaga tccctcagac ccttttagtc agtgtggaaa atctctagca   180

<210> SEQ ID NO 6
<211> LENGTH: 234
<212> TYPE: DNA
<213> ORGANISM: Artificial sequence
<220> FEATURE:
<223> OTHER INFORMATION: the sequence is synthetized

<400> SEQUENCE: 6
tgctagagat tttccacact gactaaaagg gtctgaggga tctctagtta ccagagtcac    60
acaacagacg ggcacacact acttgaagca ctcaaggcaa gctttattga ggcttaagca   120
gtgggttccc tagttagcca gagagctccc aggctcagat ctggtctaac cagagagacc   180
cagtacaagc aaaaagcaga tcttattttc gttgggagtg aattagccct tcca         234

<210> SEQ ID NO 7
<211> LENGTH: 353
<212> TYPE: DNA
<213> ORGANISM: Artificial sequence
<220> FEATURE:
<223> OTHER INFORMATION: the sequence is synthetized

<400> SEQUENCE: 7
atgggtgcga gagcgtcagt attaagcggg ggagaattag atcgcgatgg gaaaaaattc    60
ggttaaggcc agggggaaag aaaaaatata aattaaaaca tatagtatgg gcaagcaggg   120
agctagaacg attcgcagtt aatcctggcc tgttagaaac atcagaaggc tgtagacaaa   180
tactgggaca gctacaacca tcccttcaga caggatcaga gaacttaga tcattatata    240 atacagtagc aaccctctat tgtgtgcatc aaaggataga gataaaagac accaaggaag   300
ctttagacaa gatagaggaa gagcaaaaca aaagtaagac caccgcacag caa          353

<210> SEQ ID NO 8
<211> LENGTH: 233
<212> TYPE: DNA
<213> ORGANISM: Artificial sequence
<220> FEATURE:
<223> OTHER INFORMATION: the sequence is synthetized

<400> SEQUENCE: 8
aggagctttg ttccttgggt tcttgggagc agcaggaagc actatgggcg cagcctcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcc          233

<210> SEQ ID NO 9
<211> LENGTH: 489
<212> TYPE: DNA
<213> ORGANISM: Artificial sequence
<220> FEATURE:
<223> OTHER INFORMATION: the sequence is synthetized

<400> SEQUENCE: 9
tggggatttg gggttgctct ggaaaactca tttgcaccac tgctgtgcct tggaatgcta    60
gttggagtaa taaatctctg gaacagattg gaatcacacg acctggatgg agtgggacag   120
agaaattaac aattacacaa gcttaataca ctccttaatt gaagaatcgc aaaaccagca   180

```
agaaaagaat gaacaagaat tattggaatt agataaatgg gcaagtttgt ggaattggtt      240
taacataaca aattggctgt ggtatataaa attattcata atgatagtag gaggcttggt      300
aggtttaaga atagtttttg ctgtactttc tatagtgaat agagttaggc agggatattc      360
accattatcg tttcagaccc acctcccaac cccgagggga cccgacaggc ccgaaggaat      420
agaagaagaa ggtggagaga gagacagaga cagatccatt cgattagtga acggatctcg      480
acggttaac                                                              489
```

<210> SEQ ID NO 10
<211> LENGTH: 119
<212> TYPE: DNA
<213> ORGANISM: Artificial sequence
<220> FEATURE:
<223> OTHER INFORMATION: the sequence is synthetized

<400> SEQUENCE: 10

```
ttttaaaaga aaggggggga ttgggggggta cagtgcaggg gaaagaatag tagacataat       60
agcaacagac atacaaacta aagaattaca aaaacaaatt acaaaaattc aaaattta        119
```

<210> SEQ ID NO 11
<211> LENGTH: 592
<212> TYPE: DNA
<213> ORGANISM: Artificial sequence
<220> FEATURE:
<223> OTHER INFORMATION: the sequence is synthetized

<400> SEQUENCE: 11

```
aatcaacctc tggattacaa aatttgtgaa agattgactg gtattcttaa ctatgttgct       60 cctttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccact     240 ggttggggca ttgccaccac ctgtcagctc cttttcggga ctttcgcttt ccccctccct     300
attgccacgg cggaactcat cgccgcctgc cttgcccgct gctggacagg gctcggctg     360 ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttcctttc ccgcggcctg ctgccggctc tgcggcctct tccgcgtctt    540
cgccttcgcc ctcagacgag tcggatctcc ctttgggccg cctccccgcc tg            592
```

<210> SEQ ID NO 12
<211> LENGTH: 1178
<212> TYPE: DNA
<213> ORGANISM: Artificial sequence
<220> FEATURE:
<223> OTHER INFORMATION: the sequence is synthetized

<400> SEQUENCE: 12

```
gctccggtgc ccgtcagtgg gcagagcgca catcgcccac agtccccgag aagttggggg       60
gaggggtcgg caattgaacc ggtgcctaga gaaggtggcg cggggtaaac tgggaaagtg     120
atgtcgtgta ctggctccgc cttttttccg agggtggggg agaaccgtat ataagtgcag     180
tagtcgccgt gaacgttctt tttcgcaacg ggtttgccgc cagaacacag gtaagtgccg     240
tgtgtggttc ccgcgggcct ggcctctttta cgggttatgg cccttgcgtg ccttgaatta     300
cttccacctg gctgcagtac gtgattcttg atcccgagct tcgggttgga agtgggtggg     360
```

```
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaattttt gatgacctgc tgcgacgctt tttttctggc    540
aagatagtct tgtaaatgcg ggccaagatc tgcacactgg tatttcggtt tttggggccg    600
cgggcggcga cggggcccgt gcgtcccagc gcacatgttc ggcgaggcgg ggcctgcgag    660
cgcggccacc gagaatcgga cggggtagt ctcaagctgg ccggcctgct ctggtgcctg     720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg cctttccgt     900 cctcagccgt cgcttcatgt gactccactg agtaccgggc gccgtccagg cacctcgatt    960
agttctcgag cttttggagt acgtcgtctt taggttgggg ggaggggttt tatgcgatgg   1020
agtttcccca cactgagtgg gtggagacta agttaggcc agcttggcac ttgatgtaat    1080
tctccttgga atttgccctt tttgagtttg gatcttggtt cattctcaag cctcagacag   1140
tggttcaaag tttttttctt ccatttcagg tgtcgtga                           1178
```

```
<210> SEQ ID NO 13
<211> LENGTH: 63
<212> TYPE: DNA
<213> ORGANISM: Artificial sequence
<220> FEATURE:
<223> OTHER INFORMATION: the sequence is synthetized

<400> SEQUENCE: 13
atggccttac cagtgaccgc cttgctcctg ccgctggcct tgctgctcca cgccgccagg     60
ccg                                                                   63
```

```
<210> SEQ ID NO 14
<211> LENGTH: 324
<212> TYPE: DNA
<213> ORGANISM: Artificial sequence
<220> FEATURE:
<223> OTHER INFORMATION: the sequence is synthetized

<400> SEQUENCE: 14
gacatccaga tgacccagag ccctagctca ctgagcgcca gcgtgggcga cagggtgacc     60
attacctgct ccgccagcca ggacatcagc aactacctga actggtacca gcagaagccc    120
ggcaaggccc ccaagctgct gatctactac acctccaacc tgcactccgg cgtgcccagc    180
aggttcagcg gaagcggcag cggcaccgat ttcaccctga ccatctccag cctgcagccc    240
gaggacttcg ccacctacta ctgccagcag tacaggaagc tcccctggac tttcggccag    300
ggcaccaaac tggagatcaa gcgt                                            324
```

```
<210> SEQ ID NO 15
<211> LENGTH: 45
<212> TYPE: DNA
<213> ORGANISM: Artificial sequence
<220> FEATURE:
<223> OTHER INFORMATION: the sequence is synthetized

<400> SEQUENCE: 15
ggtggcggtg gctcgggcgg tggtgggtcg ggtggcggcg gatct                      45
```

```
<210> SEQ ID NO 16
<211> LENGTH: 363
```

```
<212> TYPE: DNA
<213> ORGANISM: Artificial sequence
<220> FEATURE:
<223> OTHER INFORMATION: the sequence is synthetized

<400> SEQUENCE: 16
caggtgcagc tggtccagag cggcgccgaa gtgaagaagc ccggcagctc cgtgaaagtg      60
agctgcaagg ccagcggcgg caccttcagc aactactgga tgcactgggt gaggcaggcc     120
cccggacagg gcctggagtg gatgggcgcc acctacaggg ccacagcga cacctactac     180 aaccagaagt tcaagggccg ggtgaccatc accgccgaca gagcaccag caccgcctac     240 atggaactga gcagcctcag gagcgaggac accgctgtgt attactgcgc caggggcgcc     300
atctacgacg gctacgacgt gctggacaac tggggccagg gcacactagt gaccgtgtcc     360
agc                                                                    363

<210> SEQ ID NO 17
<211> LENGTH: 141
<212> TYPE: DNA
<213> ORGANISM: Artificial sequence
<220> FEATURE:
<223> OTHER INFORMATION: the sequence is synthetized

<400> SEQUENCE: 17
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgatatcta c                                                141

<210> SEQ ID NO 18
<211> LENGTH: 66
<212> TYPE: DNA
<213> ORGANISM: Artificial sequence
<220> FEATURE:
<223> OTHER INFORMATION: the sequence is synthetized

<400> SEQUENCE: 18
atctgggcgc ccttggccgg gacttgtggg gtccttctcc tgtcactggt tatcacccct      60
tactgc                                                                 66

<210> SEQ ID NO 19
<211> LENGTH: 126
<212> TYPE: DNA
<213> ORGANISM: Artificial sequence
<220> FEATURE:
<223> OTHER INFORMATION: the sequence is synthetized

<400> SEQUENCE: 19
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 20
<211> LENGTH: 336
<212> TYPE: DNA
<213> ORGANISM: Artificial sequence
<220> FEATURE:
<223> OTHER INFORMATION: the sequence is synthetized

<400> SEQUENCE: 20
agagtgaagt tcagcaggag cgcagacgcc cccgcgtaca agcagggcca gaaccagctc      60
```

```
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336

<210> SEQ ID NO 21
<211> LENGTH: 726
<212> TYPE: DNA
<213> ORGANISM: Artificial sequence
<220> FEATURE:
<223> OTHER INFORMATION: the sequence is synthetized

<400> SEQUENCE: 21
gatattgtgc tgacccagag cccggcgagc ctggcggtga gcccgggcca gcgcgcgacc     60
attacctgcc gcgcgagcca gagcgtgagc accagcagca gcagctttat gcattggtat    120
cagcagaaac cgggccagcc gccgaaactg ctgattaaat atgcgagcaa cctgaaaagc    180
ggcgtgccgg cgcgctttag cggcagcggc agcggcaccg attttaccct gaccattaac    240
ccggtggaag cgaacgatac cgcgaactat tattgccagc atagctggga aattccgtat    300
acctttggcc agggcaccaa actggaaatt aaaggtggcg gtggctcggg cggtggtggg    360
tcgggtggcg gcggatctga agtgcagctg gtggaaagcg gcggcggcct ggtgaaaccg    420
ggcggcagcc tgcgcctgag ctgcgcggcg agcggcttta ttttcgcag ctatggcatg    480 agctgggtgc gccaggcgcc gggcaaaggc ctggaatggg tggcgagcat tagcagcggc    540
ggcagcacct attatccgga tagcgtgaaa ggccgcttta ccattagccg cgataacgcg    600
aaaaacagcc tgtatctgca gatgaacagc ctgcgcgcgg aagataccgc ggtgtatgat    660
tgcgcgcgcg gctatgatag cggctttgcg tattggggcc agggcaccct ggtgaccgtg    720
agcagc                                                               726

<210> SEQ ID NO 22
<211> LENGTH: 717
<212> TYPE: DNA
<213> ORGANISM: Artificial sequence
<220> FEATURE:
<223> OTHER INFORMATION: the sequence is synthetized

<400> SEQUENCE: 22
gatattcaga tgacccagag cccgagcagc ctgagcgcga gcgtgggcga tcgcgtgacc     60
attagctgcc gcgcgagcca gagcgtgagc accagcagct atagctatgt gcattggtat    120
cagcaggcgc cgaaactgct gatttattat gcggcgaacc gctataccgg cgtgccggat    180
cgctttagcg cgcgctttag cggcagcggc agcggcaccg attttaccct gaacattcat    240
ccggtggaag aagaatattt tgccagcag gattatacca gcccgtatac ctttggccag    300
ggcaccaaac tggaaattaa aggtggcggt ggctcgggcg gtggtgggtc gggtggcggc    360
ggatctcaga ttaccctgaa agaaagcggc ccgacctg tgaaaccgac ccagaccctg    420
accctgacct gcgcggcgag cggctttagc tttagcagct atggcatgag ctgggtgcgc    480 cagacccgg aagcgctgga atggctgggc gtgatttggc gcggcgtgac caccgattat    540
aacgcggcgt ttaaaggccg ctttaccatt agccgcgata acgcgcgcaa cattctgtat    600
ctgcagatga gcagcctgaa catggatccg gtggataccg cgacctatta ttgcgcgcgc    660
ctgggctttt atgcgatgga ttattggggc cagggcaccc tggtgaccgt gagcagc      717
```

<210> SEQ ID NO 23
<211> LENGTH: 723
<212> TYPE: DNA
<213> ORGANISM: Artificial sequence
<220> FEATURE:
<223> OTHER INFORMATION: the sequence is synthetized

<400> SEQUENCE: 23

```
gatattgtgc tgacccagag cccggcgagc ctggcggtga gcctgggcca gcgcgcgacc      60
attacctgca aagcgagcca gagcgtgagc aacgatgtgg cgtggtatca gcagaaaccg     120
ggcaaaaaac cgggccagcc gccgaaactg ctgattaaat atgcgagcaa cctggaaagc     180
ggcgtgccgg cagcggcta tggcaccgat tttaccttta ccattagcag cctgcagccg      240
gaagatattg cgaccgatac cgcgacctat tattgccagc atagctggga aattccgtat     300
acctttggcg gcggcaccaa actggaaatt aaaggtggcg gtggctcggg cggtggtggg     360
tcgggtggcg gcggatctga agaaaaactg gtggaaagcg gcggcggcct ggtgaaaccg     420
ggcggcagcc tgaaactgag ctgcaccgtg agcggcttta gcctgagcac ctatggcgtg     480
cattggattc gccagccgcc gggcaaaaaa cgcctggaat gggtggcgag cattagcagc     540
ggcggcagca tttattatcc ggatagcgtg atgagccgcc tgaccattac caaagataac     600
agcaaaaacc aggtggtgct gaccatgaac cgcagcgaag ataccgcgat gtattattgc     660
gcgcgcggct atgatgcggg cttttgcgttt tggggccagg gcaccctggt gaccgcgagc     720
gcg                                                                   723
```

<210> SEQ ID NO 24
<211> LENGTH: 699
<212> TYPE: DNA
<213> ORGANISM: Artificial sequence
<220> FEATURE:
<223> OTHER INFORMATION: the sequence is synthetized

<400> SEQUENCE: 24

```
ttgttctgga ttcctgcttc catcagtgat gttgtgatga cccaaactgt cagtcttgga      60
gatcaagctt ccatctcttg cagatctagt cagaaccttg tacacaacaa tggaaacacc     120
tatttatatt ggttcctgca gaagtcaggc cagtctccaa agctcctgat ttatagggct     180
tccatccgat tttctggggt cccagacagg ttcagtggca gtggatcaga gacagatttc     240
acactcaaga tcagcagagt ggaggcttat ttctgctttc aaggtacaca tgttccgtgg     300
acgttcggtg aggcaccaa gctggaaatc aaaggtggcg gtggctcggg cggtggtggg      360
tcgggtggcg gcggatctga ggtgctgctg caacagtctg gacctgagct ggtgaagata     420
cccctgcaagg cttctggata cacattcact gactacaaca tggactggat gaagcagagc     480
catggaaaga gccttgagtg gattggagat attaatccta gagtggtaa ttccatctac      540
aaccagaagt tcaagggcaa ggccacactg actgtagaca gtcctccag cacagcctac      600
atggagctcc gcagcctgac atctgaggac actgcagtct atgactggtc tgcctggttt     660
gctttctggg gccaagggac tctggtctct gtctctgca                            699
```

<210> SEQ ID NO 25
<211> LENGTH: 575
<212> TYPE: DNA
<213> ORGANISM: Artificial sequence
<220> FEATURE:
<223> OTHER INFORMATION: the sequence is synthetized

<400> SEQUENCE: 25

| | | |
|---|---|---|
| gcccctctcc ctccccccccc cctaacgtta ctggccgaag ccgcttggaa taaggccggt | 60 |
| gtgcgtttgt ctatatgtta ttttccacca tattgccgtc ttttggcaat gtgagggccc | 120 |
| ggaaacctgg ccctgtcttc ttgacgagca ttcctagggg tctttcccct ctcgccaaag | 180 |
| gaatgcaagg tctgttgaat gtcgtgaagg aagcagttcc tctggaagct tcttgaagac | 240 |
| aaacaacgtc tgtagcgacc cttttgcagg agcggaaccc cccacctggc gacaggtgcc | 300 |
| tctgcggcca aaagccacgt gtataagata cacctgcaaa ggcggcacaa ccccagtgcc | 360 |
| acgttgtgag ttggatagtt gtggaaagag tcaaatggct cacctcaagc gtattcaaca | 420 |
| aggggctgaa ggatgcccag aaggtacccc attgtatggg atctgatctg gggcctcggt | 480 |
| gcacatgctt tacatgtgtt tagtcgaggt taaaaaacgt ctaggccccc cgaaccacgg | 540 |
| ggacgtggtt ttcctttgaa aaacacgatg ataat | 575 |

<210> SEQ ID NO 26
<211> LENGTH: 87
<212> TYPE: DNA
<213> ORGANISM: Artificial sequence
<220> FEATURE:
<223> OTHER INFORMATION: the sequence is synthetized

<400> SEQUENCE: 26

| | | |
|---|---|---|
| atgaactcct tctccacaag cgccttcggt ccagttgcct tctccctggg gctgctcctg | 60 |
| gtgttgcctg ctgccttccc tgcccca | 87 |

<210> SEQ ID NO 27
<211> LENGTH: 696
<212> TYPE: DNA
<213> ORGANISM: Artificial sequence
<220> FEATURE:
<223> OTHER INFORMATION: the sequence is synthetized

<400> SEQUENCE: 27

| | | |
|---|---|---|
| gaaccgaaaa gctgcgataa aacccatacc tgcccgccgt gcccggcgcc ggaactgctg | 60 |
| ggcggcccga gcgtgtttct gtttccgccg aaaccgaaag ataccctgat gattagccgc | 120 |
| accccggaag tgacctgcgt ggtggtggat gtgagccatg aagatccgga agtgaaattt | 180 |
| aactggtatg tggatggcgt ggaagtgcat aacgcgaaaa ccaaaccgcg cgaagaacag | 240 |
| tataacagca cctatcgcgt ggtgagcgtg ctgaccgtgc tgcatcagga ttggctgaac | 300 |
| ggcaaagaat ataaatgcaa agtgagcaac aaagcgctgc cggcgccgat tgaaaaaacc | 360 |
| attagcaaag cgaaaggcca gccgcgcgaa ccgcaggtgt ataccctgcc gccgagccgc | 420 |
| gaagaaatga ccaaaaacca ggtgagcctg acctgcctgg tgaaaggctt ttatccgagc | 480 |
| gatattgcgg tggaatggga aagcaacggc cagccggaaa acaactataa aaccacccccg | 540 |
| ccggtgctgg atagcgatgg cagcttttttt ctgtatagca aactgaccgt ggataaaagc | 600 |
| cgctggcagc agggcaacgt gtttagctgc agcgtgatgc atgaagcgct gcataaccat | 660 |
| tatacccaga aaagcctgag cctgagcccg ggcaaa | 696 |

<210> SEQ ID NO 28
<211> LENGTH: 123
<212> TYPE: DNA
<213> ORGANISM: Artificial sequence
<220> FEATURE:
<223> OTHER INFORMATION: the sequence is synthetized

<400> SEQUENCE: 28
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 29
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 29
attcaaaatt ttatcgatgc tccggtgccc gtcagt                              36

<210> SEQ ID NO 30
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 30
tcacgacacc tgaaatggaa ga                                             22

<210> SEQ ID NO 31
<211> LENGTH: 42
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 31
ggtgtcgtga ggatccgcca ccatggcctt accagtgacc gc                       42

<210> SEQ ID NO 32
<211> LENGTH: 30
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 32
ggtcatctgg atgtccggcc tggcggcgtg                                     30

<210> SEQ ID NO 33
<211> LENGTH: 37
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 33

```
cacgccgcca ggccggacat ccagatgacc cagagcc                              37

<210> SEQ ID NO 34
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 34
acgcttgatc tccagtttgg t                                               21

<210> SEQ ID NO 35
<211> LENGTH: 81
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 35
actggagatc aagcgtggtg gcggtggctc gggcggtggt gggtcgggtg gcggcggatc    60
tcaggtgcag ctggtccaga g                                              81

<210> SEQ ID NO 36
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 36
gctggacacg gtcactagtg tg                                              22

<210> SEQ ID NO 37
<211> LENGTH: 33
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 37
agtgaccgtg tccagcacca cgacgccagc gcc                                  33

<210> SEQ ID NO 38
<211> LENGTH: 23
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 38
gtagatatca caggcgaagt cca                                             23
```

<210> SEQ ID NO 39
<211> LENGTH: 33
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 39
cgcctgtgat atctacatct gggcgccctt ggc                33

<210> SEQ ID NO 40
<211> LENGTH: 39
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 40
tctttctgcc ccgtttgcag taaagggtga taaccagtg          39

<210> SEQ ID NO 41
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 41
aaacggggca gaaagaaact c                             21

<210> SEQ ID NO 42
<211> LENGTH: 40
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 42
tgctgaactt cactctcagt tcacatcctc cttcttcttc         40

<210> SEQ ID NO 43
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 43
agagtgaagt tcagcaggag cg                            22

<210> SEQ ID NO 44
<211> LENGTH: 34

```
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 44
ggagaggggc gtcgacttag cgaggggca gggc                                34

<210> SEQ ID NO 45
<211> LENGTH: 34
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 45
gccctgcccc ctcgctaagc ccctctccct cccc                               34

<210> SEQ ID NO 46
<211> LENGTH: 79
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 46
ccagggagaa ggcaactgga ccgaaggcgc ttgtggagaa ggagttcatg gtggcattat   60
catcgtgttt ttcaaagga                                                79

<210> SEQ ID NO 47
<211> LENGTH: 74
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 47
gttgccttct ccctggggct gctcctggtg ttgcctgctg ccttccctgc cccagatatt   60
gtgctgaccc agag                                                     74

<210> SEQ ID NO 48
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 48
gcagcttttc ggttcgctgc tcacggtcac cagggt                             36

<210> SEQ ID NO 49
<211> LENGTH: 75
```

```
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 49
gttgccttct ccctggggct gctcctggtg ttgcctgctg ccttccctgc cccagatatt    60
cagatgaccc agagc                                                    75

<210> SEQ ID NO 50
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 50
gcagcttttc ggttcgctgc tcacggtcac cagggt                             36

<210> SEQ ID NO 51
<211> LENGTH: 75
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 51
gttgccttct ccctggggct gctcctggtg ttgcctgctg ccttccctgc cccagatatt    60
gtgctgaccc agagc                                                    75

<210> SEQ ID NO 52
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 52
gcagcttttc ggttccgcgc tcgcggtcac cagggt                             36

<210> SEQ ID NO 53
<211> LENGTH: 76
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 53
gttgccttct ccctggggct gctcctggtg ttgcctgctg ccttccctgc cccattgttc    60
tggattcctg cttcca                                                   76
```

```
<210> SEQ ID NO 54
<211> LENGTH: 36
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 54
gcagcttttc ggttctgcag agacagagac cagagt                          36

<210> SEQ ID NO 55
<211> LENGTH: 23
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 55
gaaccgaaaa gctgcgataa aac                                        23

<210> SEQ ID NO 56
<211> LENGTH: 38
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 56
ctagcaatct agaggttatt tgcccgggct caggctca                        38

<210> SEQ ID NO 57
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 57
cctttccggg actttcgctt t                                          21

<210> SEQ ID NO 58
<211> LENGTH: 20
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 58
gcagaatcca ggtggcaaca                                            20

<210> SEQ ID NO 59
<211> LENGTH: 21
<212> TYPE: DNA
<213> ORGANISM: Artificial sequence
```

<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 59
catgtacgtt gctatccagg c                           21

<210> SEQ ID NO 60
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 60
ctccttaatg tcacgcacga t                           21

<210> SEQ ID NO 61
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 61
gacttgtggg gtccttctcc t                           21

<210> SEQ ID NO 62
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 62
gcagctacag ccatcttcct c                           21

<210> SEQ ID NO 63
<211> LENGTH: 19
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 63
tgcagcttct ccaacacat                              19

<210> SEQ ID NO 64
<211> LENGTH: 18
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 64
cttgtccgtc tggttgct                                          18

<210> SEQ ID NO 65
<211> LENGTH: 23
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 65
caccaggatg ctcacattta agt                                    23

<210> SEQ ID NO 66
<211> LENGTH: 23
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 66
gtccctgggt cttaagtgaa agt                                    23

<210> SEQ ID NO 67
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 67
gacattggaa atgtgaacat gt                                     22

<210> SEQ ID NO 68
<211> LENGTH: 19
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 68
cacagctggg gtttggtga                                         19

<210> SEQ ID NO 69
<211> LENGTH: 18
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 69

```
tctctaatca gccctctg                                                    18

<210> SEQ ID NO 70
<211> LENGTH: 18
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 70
gggtttgcta caacatgg                                                    18

<210> SEQ ID NO 71
<211> LENGTH: 21
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 71
gactaattat tcggtaactg a                                                21

<210> SEQ ID NO 72
<211> LENGTH: 22
<212> TYPE: DNA
<213> ORGANISM: Artificial sequence
<220> FEATURE:
<223> OTHER INFORMATION: the sequence is synthetized
<220> FEATURE:
<221> NAME/KEY: misc_feature
<223> OTHER INFORMATION: Primer

<400> SEQUENCE: 72
gatgctcttc gacctcgaaa ca                                               22
```